US012751601B2

(12) United States Patent
Hammer et al.

(10) Patent No.: US 12,751,601 B2
(45) Date of Patent: Oct. 6, 2026

(54) ULTRASONIC ATTACHMENT ASSEMBLY FOR AN ENDOSCOPE

(71) Applicant: ENDOSOUND, INC., Portland, OR (US)

(72) Inventors: Jeremy Andrew Hammer, Portland, OR (US); Scott Sutherland Corbett, III, Portland, OR (US); Peter D. Hoffman, Portland, OR (US); Kevin Josh Cohn, Cornelius, NC (US); Stephen Edward Steinberg, Boca Raton, FL (US); William J. McDonough, Portland, OR (US)

(73) Assignee: ENDOSOUND, INC., Portland, OR (US)

( * ) Notice: Subject to any disclaimer, the term of this patent is extended or adjusted under 35 U.S.C. 154(b) by 0 days.

(21) Appl. No.: 19/106,695

(22) PCT Filed: Aug. 23, 2023

(86) PCT No.: PCT/US2023/072754
§ 371 (c)(1),
(2) Date: Feb. 26, 2025

(87) PCT Pub. No.: WO2024/050268
PCT Pub. Date: Mar. 7, 2024

(65) Prior Publication Data
US 2026/0000278 A1 Jan. 1, 2026

Related U.S. Application Data

(60) Provisional application No. 63/373,724, filed on Aug. 28, 2022.

(51) Int. Cl.
*A61B 1/00* (2006.01)
*A61B 1/018* (2006.01)
(Continued)

(52) U.S. Cl.
CPC ........ *A61B 1/0014* (2013.01); *A61B 1/00098* (2013.01); *A61B 1/00101* (2013.01);
(Continued)

(58) Field of Classification Search
CPC .............. A61B 1/0014; A61B 1/00098; A61B 1/00101; A61B 1/00135; A61B 1/018; A61B 1/273; A61B 8/4209; A61B 8/4272
See application file for complete search history.

(56) References Cited

U.S. PATENT DOCUMENTS 6,210,330 B1 4/2001 Tepper
6,461,304 B1 * 10/2002 Tanaka ................ A61B 8/4488 600/462
(Continued)

FOREIGN PATENT DOCUMENTS

WO 2022155280 A1 7/2022
WO 2024050268 A1 3/2024

OTHER PUBLICATIONS

International Search Report and Written Opinion for corresponding International PCT Application No. PCT/US2023/072754, dated Feb. 6, 2024.

*Primary Examiner* — Timothy J Neal
(74) *Attorney, Agent, or Firm* — K&L Gates LLP

(57) ABSTRACT

Various ultrasonic attachment assemblies for endoscopes are disclosed. In one aspect, the ultrasonic attachment assembly can include an ultrasonic transducer and a clip. The ultrasonic transducer includes a transducer lens and a transducer body. The clip is configured to be removably secured to a distal end of an endoscope and hold the transducer body such that the transducer lens is positioned distally with respect to the distal end of the endoscope. In another aspect, the ultrasonic attachment assembly can include an ultrasonic transducer and a sleeve. The ultrasonic transducer includes a transducer lens and a transducer body. The sleeve is
(Continued)

configured to be positioned on a distal end of an endoscope and hold the transducer body such that the transducer lens is positioned distally with respect to the distal end of the endoscope.

20 Claims, 20 Drawing Sheets

(51) Int. Cl.
*A61B 1/273* (2006.01)
*A61B 8/00* (2006.01)

(52) U.S. Cl.
CPC .......... *A61B 1/00135* (2013.01); *A61B 1/018* (2013.01); *A61B 1/273* (2013.01); *A61B 8/4209* (2013.01); *A61B 8/4272* (2013.01)

(56) References Cited

U.S. PATENT DOCUMENTS

| | | | | |
|---|---|---|---|---|
| 2009/0005689 | A1* | 1/2009 | Kodama ................ | A61B 8/445 600/466 |
| 2011/0152618 | A1* | 6/2011 | Surti .................. | A61B 1/00137 600/129 |
| 2018/0235453 | A1 | 8/2018 | Morimoto et al. | |
| 2019/0357883 | A1* | 11/2019 | Steinberg ........... | A61B 1/00101 |
| 2021/0113067 | A1 | 4/2021 | Hosogoe | |

* cited by examiner

ULTRASONIC ATTACHMENT ASSEMBLY FOR AN ENDOSCOPE

CROSS-REFERENCE TO RELATED APPLICATIONS

This application is a U.S. National Stage Entry under 35 U.S.C. § 371 of International Patent Application No. PCT/US2023/072754, titled ULTRASONIC ATTACHMENT ASSEMBLY FOR AN ENDOSCOPE, filed Aug. 23, 2023, which claims benefit under 35 U.S.C. § 119(e) to U.S. Provisional Patent Application No. 63/373,724, titled ULTRASONIC ATTACHMENT ASSEMBLY FOR AN ENDOSCOPE, filed Aug. 28, 2022, the entire disclosures of which are hereby incorporated by reference herein.

FIELD

The present disclosure is generally related to endoscopic ultrasonography, and in some aspects, ultrasonic attachment assemblies that can be used to convert to traditional endoscopes to include an ultrasonic device for performing endoscopic ultrasound procedures.

BACKGROUND

Endoscopy generally involves a doctor inserting a tube (e.g., an endoscope) into an interior cavity of the body of a patient for diagnosis and treatment. For example, an endoscope may be inserted through the patient's throat and esophagus to access the stomach and/or the upper portion of the small intestine. Endoscopes typically include a visual light-based imaging device (e.g., a camera) that allows the doctor to visualize the interior cavity of the patient. However, using only the visual light-based imaging device, the doctor is unable to see tissue and other objects that are outside of the interior cavity into which the endoscope is inserted (e.g., objects outside of the upper digestive tract such as the pancreas, liver, etc.).

Ultrasonography generally involves the use of an ultrasonic device (e.g., an ultrasonic transducer) to visualize objects (e.g., organs) inside of the body. The ultrasonic device generates high-frequency sound waves (e.g., ultrasonic waves) that can be directed towards an object of interest within the body of a patient, for example, by placing the device on the patient's skin overlying the object. The ultrasonic device can detect sound waves that are reflected by the object and use these reflected sound waves to create an ultrasonic image of the object. Thus, an ultrasonic device can be used to visualize objects that would otherwise be obstructed.

Endoscopic ultrasonography combines endoscopy with ultrasonography. Endoscopic ultrasonography typically involves the use of an echoendoscope (e.g., an endoscopic that includes an ultrasonic transducer). The echoendoscope allows the ultrasonic device to be inserted into a cavity of the body of the patient. Thus, the echoendoscope can position the ultrasonic device closer to an object of interest within the body compared to placing a traditional ultrasonic device on the patient's skin. This closer positioning can allow more detailed images of the object to be captured. Moreover, the echoendoscope can allow a doctor to view objects that are not viewable using an endoscope that relies solely on visual light-based imaging. Accordingly, echoendoscopes can greatly improve the ability to visualize organs and other objects within the body, obtain tissue samples, implement treatments, etc. However, because echoendoscope systems can be very expensive (e.g., greater than $300,000 for a complete system), their availability is often restricted to major hospitals. Conversely, traditional endoscopes are generally available in physicians' offices, outpatient surgery centers, and virtually all hospitals. Accordingly, there is a need for systems, devices, and methods for affordably converting these widely available endoscopes to include an ultrasonic device.

Furthermore, one type of specialized endoscope is a duodenoscope. Duodenoscopes are typically used to perform endoscopic retrograde cholangiography and pancreatography (ERCP). To perform ERCP, the duodenoscope is inserted into the duodenum (the upper part of the small intestine) to access the bile duct, which empties into the duodenum. A catheter can be extended from the distal end of the duodenoscope and used to inject contrast dye into the bile duct for radiographic imaging. Although duodenoscopes generally include a video camera and a light configured to help visualize the pancreatic/bile duct entry into the duodenum (e.g., the papilla of Vater), using an ultrasonic device can greatly improve the doctor's ability to visualize the pancreas, bile duce and surrounding structures within the body. Accordingly, there is a need for systems, devices, and methods for converting duodenoscopes to include an ultrasonic device.

Yet further, endoscopes must be thoroughly cleaned and disinfected between procedures to avoid patient contamination. However, in recent years, various issues related to cleaning and disinfecting endoscopes, and duodenoscopes in particular, have been a cause for concern. For example, the small spaces defined by the elevator actuation mechanism of the duodenoscope can make it difficult to properly clean and disinfect the duodenoscope between uses. Accordingly, there is a need for systems, devices, and methods for converting traditional endoscopes (e.g., duodenoscopes) to include an ultrasonic device while also ensuring that the ultrasonic device and any components used to attach the ultrasonic device can be properly disinfected and/or affordably disposed of. Various aspects of the present disclosure provide ultrasonic attachment assemblies that can be used to convert to existing endoscopes (e.g., existing duodenoscopes) to include an ultrasonic device.

SUMMARY

The following summary is provided to facilitate an understanding of some of the innovative features unique to the aspects disclosed herein and is not intended to be a full description. A full appreciation of the various aspects disclosed herein can be gained by taking the entire specification, claims, and abstract as a whole.

In various aspects, an ultrasonic attachment assembly is disclosed. The ultrasonic attachment assembly can include an ultrasonic transducer and a clip. The transducer includes a transducer lens and a transducer body. The transducer lens has a field of view. The clip is configured to be removably secured to a distal end of a duodenoscope including an elevator channel. The distal end of the duodenoscope defines a central axis and the elevator channel defines an elevator channel axis that is offset from the central axis. The clip includes a clip body and a cavity formed in the clip body. The cavity is configured to hold the transducer body when the clip is secured to the distal end of the duodenoscope such that the transducer lens is positioned distally with respect to the distal end of the duodenoscope and such that the field of view is centered along the elevator channel axis.

In various aspects, an ultrasonic attachment assembly is disclosed. The ultrasonic assembly can include an ultrasonic transducer and a sleeve. The ultrasonic transducer includes a transducer lens and a transducer body. The sleeve is configured to be positioned on a distal end of a duodenoscope by removably sliding the sleeve over the distal end of the duodenoscope. The duodenoscope includes an elevator channel. The distal end of the duodenoscope defines a central axis and the elevator channel defines an elevator channel axis that is offset from the central axis. The sleeve is further configured to hold the transducer body when the sleeve is positioned on the distal end of the duodenoscope such that the transducer lens is positioned distally with respect to the distal end of the duodenoscope and such that the field of view is centered along the elevator channel axis.

In various aspects, an ultrasonic attachment assembly is disclosed. The ultrasonic attachment assembly includes an ultrasonic transducer and a transducer attachment cap. The ultrasonic transducer includes a transducer lens and a transducer body. The transducer attachment cap is configured to removably attach to a distal end of a duodenoscope configured to accept a disposable cap. The transducer attachment cap can be used instead of the disposable cap and is configured to hold the transducer body such that the transducer lens is positioned distally with respect to the distal end of the duodenoscope when the transducer attachment cap is attached to the distal end of the duodenoscope.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of any of the aspects disclosed herein.

BRIEF DESCRIPTION OF THE DRAWINGS

The various aspects described herein, together with objects and advantages thereof, may best be understood by reference to the following description, taken in conjunction with the accompanying drawings as follows.

Figure 1:
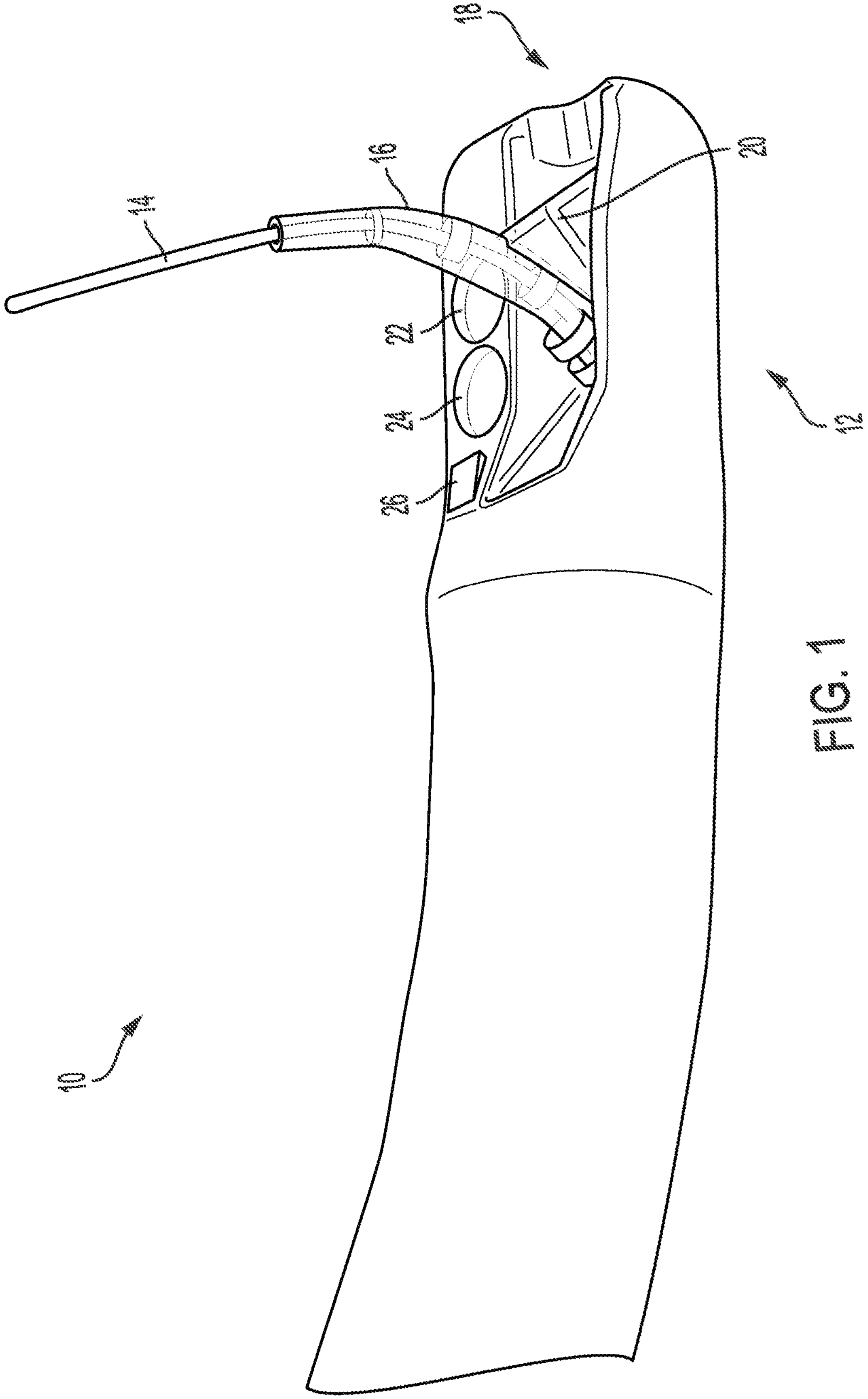
FIG. 1 illustrates a perspective view of the distal end of a duodenoscope, according to at least one non-limiting aspect of this disclosure.

Corresponding reference characters indicate corresponding parts throughout the several views. The exemplifications set out herein illustrate various aspects of the present disclosure, in one form, and such exemplifications are not to be construed as limiting the scope of any of the aspects disclosed herein.

DETAILED DESCRIPTION

Applicant of the present application owns the following U.S. Patent Applications, the disclosure of each of which is herein incorporated by reference in its respective entirety:

U.S. patent application Ser. No. 15/951,347, entitled STEERABLE ULTRASOUND ATTACHMENT FOR ENDOSCOPE, filed Apr. 12, 2018, now U.S. Pat. No. 10,363,014; and U.S. patent application Ser. No. 17/193,553, entitled STEERABLE ULTRASOUND ATTACHMENT FOR ENDOSCOPE, filed Mar. 5, 2021, now U.S. Patent Application Publication No. 2021/0212662.

Numerous specific details are set forth to provide a thorough understanding of the overall structure, function, manufacture, and use of the aspects as described in the disclosure and illustrated in the accompanying drawings. Well-known operations, components, and elements have not been described in detail so as not to obscure the aspects described in the specification. The reader will understand that the aspects described and illustrated herein are non-limiting examples, and thus, it can be appreciated that the specific structural and functional details disclosed herein may be representative and illustrative. Variations and changes thereto may be made without departing from the scope of the claims.

In the following description, like reference characters designate like or corresponding parts throughout the several views of the drawings. Also in the following description, it is to be understood that such terms as "forward," "rearward," "left," "right," "above," "below," "upwardly," "downwardly," "top," "bottom," "side," and the like are words of convenience and are not to be construed as limiting terms.

FIG. 1 illustrates a perspective view of the distal end 12 of a duodenoscope 10. In the non-limiting aspect of FIG. 1, the duodenoscope 10 is shown with a catheter 14 extending from a catheter tube 16. As explained above, duodenoscopes can be used to perform endoscopic retrograde cholangiopancreatography (ERCP). To perform ERCP, the distal end 12 of the duodenoscope 10 is inserted into the duodenum. The catheter 14 can be advanced through the catheter tube 16 and into the bile duct via the papilla of Vater. Further, contrast dye can be injected into the bile duct via the catheter tube 16 to assist with viewing various structures using radiography. In other aspects, the duodenoscope 10 can include different and/or additional instrumentation. For example, a needle, biopsy forceps, and/or other instrumentation may be advanced through the catheter tube 16 and/or other channels that extend along the length of the duodenoscope 10.

The duodenoscope 10 can include an elevator channel 18 (sometimes referred to as an instrument channel) and an elevator mechanism 20. As the catheter tube 16 is advanced through the duodenoscope 10, it exits the distal end 12 via the elevator channel 18. The elevator mechanism 20 can be actuated to control the angle at which the catheter tube 16 and other instrumentation exits the distal end 12 of the duodenoscope 10.

In some aspects, the distal end 12 of the duodenoscope 10 can include a light 22, a camera 24, and/or an air/water port 26. The light 22 and camera 24 can be used for visual light-based imaging of areas proximate to the distal end 12 of the duodenoscope 10. The air/water port 26 can have various functions, such as expelling water to clean the lens of the camera 24. As mentioned above, endoscopes (e.g., duodenoscopes) must be thoroughly cleaned and disinfected between procedures to avoid patient contamination. In some aspects, the small spaces defined by the elevator channel 18 and the elevator mechanism 20 can make the duodenoscope 10 difficult to thoroughly clean and disinfect.

Figure 2:
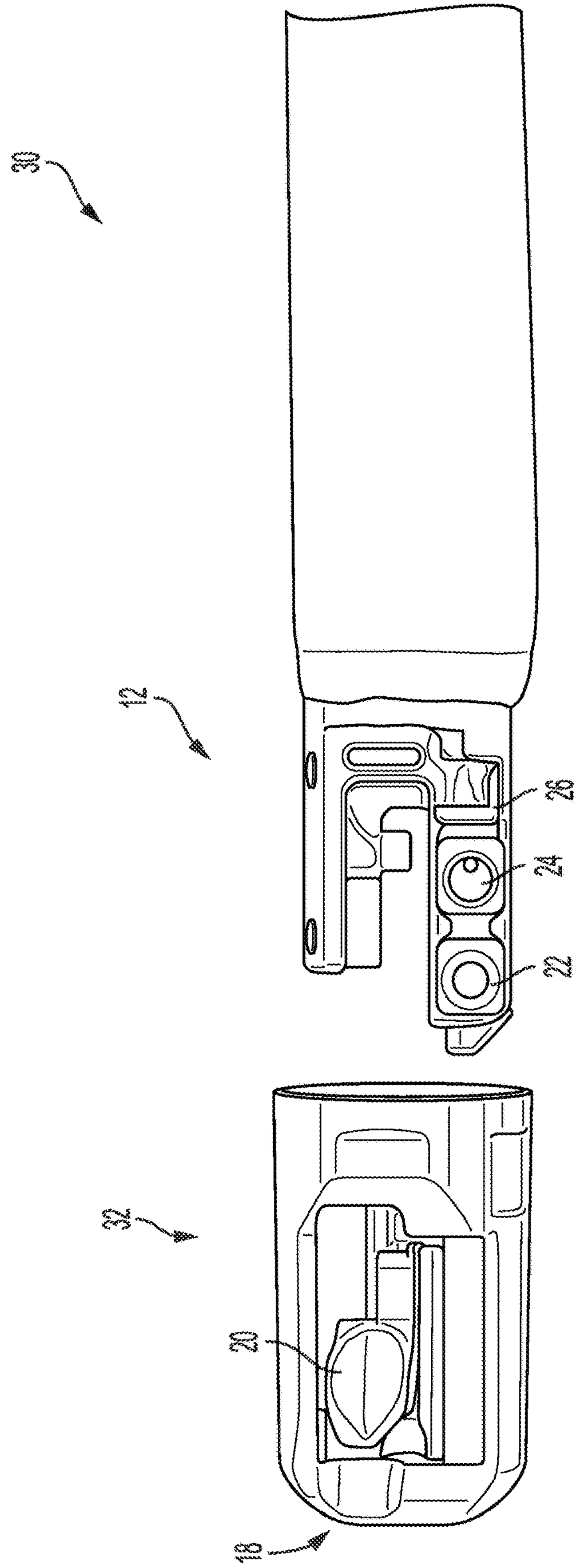
FIG. 2 illustrates an exploded view of the distal end of a duodenoscope having a removable cap, according to at least one non-limiting aspect of this disclosure.

FIG. 2 illustrates an exploded view of the distal end 12 of a duodenoscope 30 having a removable cap 32. The removable cap 32 is disposable. Thus, a new removable cap 32 can be used for each procedure that is performed using the duodenoscope 30. Furthermore, the elevator mechanism 20 can be included as part of the removable cap 32. Accordingly, using the removable cap 32 can eliminate various difficulties associated with cleaning the elevator mechanism 20 and other small spaces defined by the elevator channel 18, as shown in FIG. 1.

FIGS. 3A-14B illustrate various ultrasonic attachment assemblies (e.g., ultrasonic attachment assemblies 100, 200, 300, 400, 500, 600, 700, 800, 900, 1000, 1100, and 1200) that can be positioned on the distal end of an endoscope. Furthermore, the ultrasonic attachment assemblies illustrated by FIGS. 3A-14B can be configured to convert an existing endoscope to include ultrasonic imaging capabilities. Although some of FIGS. 3A-14B depict the ultrasonic attachment assembly positioned on the distal end 12 of duodenoscope 10 and/or duodenoscope 30, the ultrasonic attachment assemblies disclosed herein may be configured to be used with any type of endoscope (e.g., any type of duodenoscope). Persons of ordinary skill in the art will appreciate that any aspect disclosed herein with respect to a specific ultrasonic attachment assembly can be employed by any of the other the other ultrasonic attachment assemblies disclosed herein. Furthermore, corresponding reference characters indicate corresponding parts throughout the several views shown in FIGS. 3A-14B. Accordingly, aspects of an ultrasonic attachment assembly described with respect to a particular reference character can be applicable to any of the several views shown in FIGS. 3A-14B where that reference character appears.

Referring now to FIGS. 3A-3D, the ultrasonic attachment assembly 100 can be positioned on the distal end 12 of the duodenoscope 10. The ultrasonic attachment assembly 100 includes an ultrasonic transducer 110, a clip 130, and a sleeve 140. The ultrasonic transducer 110 can include a transducer body 112 and a transducer lens 114 (e.g., an acoustic lens). In some aspects, the ultrasonic transducer 110 can employ a capacitive micromachined ultrasonic transducer (CMUT). In other aspects, the ultrasonic transducer 110 can employ a piezoelectric transducer. In yet other aspects, the ultrasonic transducer 110 may be configured to include various components of the ultrasound assembly (e.g., the imaging head, the resiliently flexible neck) described in the aforementioned U.S. Patent Publication No. US2021/021266, titled STEERABLE ULTRASOUND ATTACHMENT FOR ENDOSCOPE, filed Mar. 5, 2012, which is herein incorporated by reference in its entirety.

In the non-limiting aspect of FIGS. 3A-3D, the transducer body 112 can be constructed from an elastomeric material (e.g., an elastic polymer). For example, transducer body 112 may be constructed from an elastomeric material that enables the transducer lens 114 to be positioned with respect to the distal end 12 of the duodenoscope 10 by bending and/or angling the transducer body 112. In some aspects, the elastomeric material can include at least one of a silicone, a fluoroelastomer, and/or ethylene propylene, amongst others. In some aspects, the elastomeric material can be characterized as having a low elastic modulus and, according to some non-limiting aspects, can include a Shore A Durometer measure of greater than or equal to OA and less than or equal to 100A.

Referring still to FIGS. 3A-3D, the clip 130 can include a clip body 131. The clip body 131 is configured to be positioned over the distal end 12 of the duodenoscope 10.

Further, the clip body 131 can define a cavity 133 that is configured to support transducer body 112. Accordingly, when the clip 130 is placed over the distal end 12 of the duodenoscope 10, the cavity 133 can hold the transducer body such that the transducer lens 114 is positioned distally with respect to the distal end 12 of the duodenoscope.

Figure 3A:
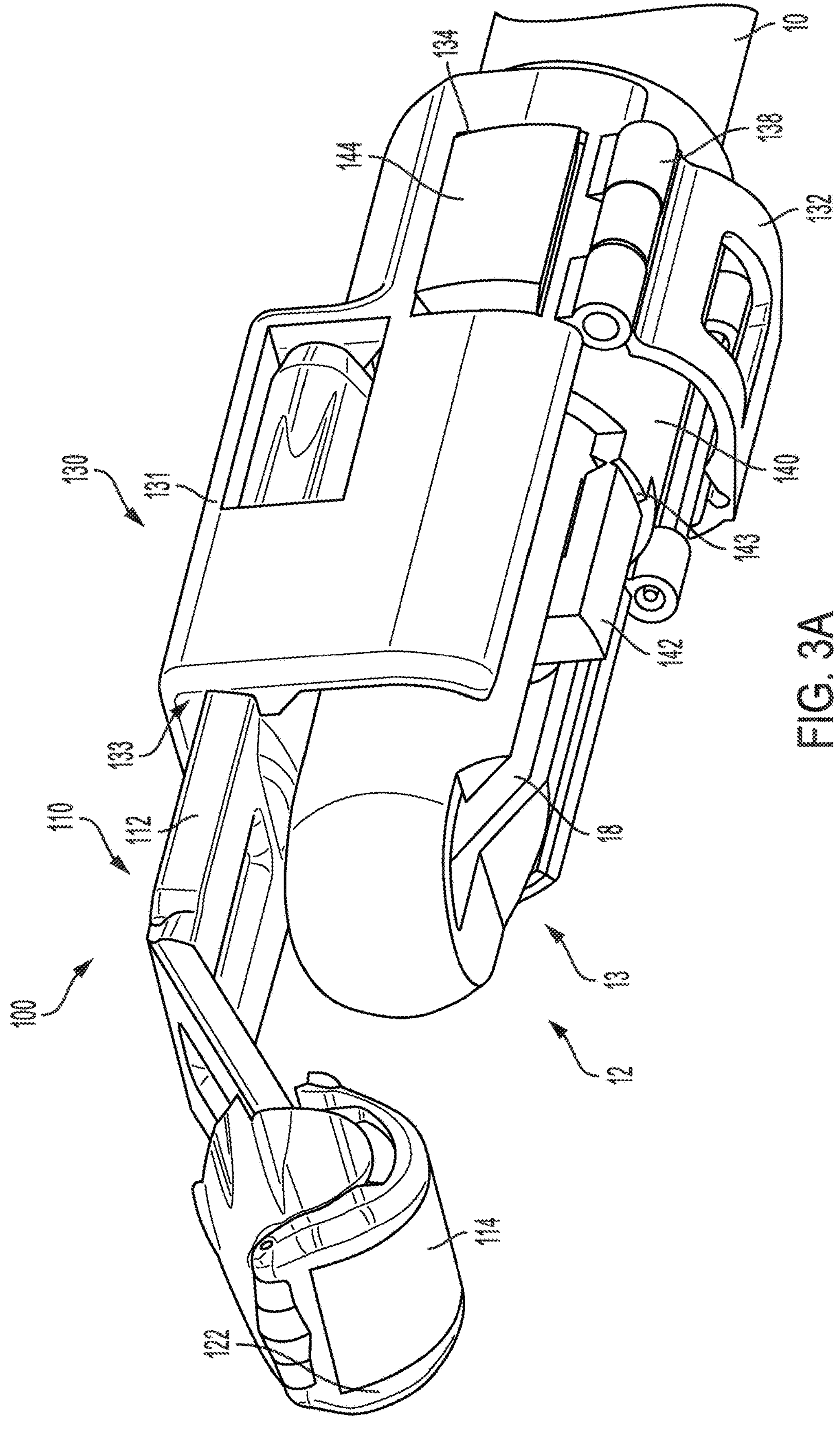
FIG. 3A illustrates a perspective view of an ultrasonic attachment assembly positioned on the distal end of a duodenoscope, according to at least one non-limiting aspect of this disclosure.

The clip 130 and the cavity 133 can be configured to laterally position the transducer lens 114 with respect to the duodenoscope 10. For example, FIG. 3C shows a bottom view of the ultrasonic assembly 100 without the duodenoscope 10. The axis UA is defined by the center of the field of view of the transducer lens 114. When the ultrasonic transducer 110 is held by the clip 130, the location of the axis UA is determined based on the configuration of the cavity 133. Further, FIG. 3D shows a detailed view bottom of the ultrasonic assembly 100 (including the distal end 12 of the duodenoscope 10), the center axis CA of the duodenoscope 10, and an axis EA defined by the elevator channel 18. The elevator channel 18 axis EA is offset from the center axis CA of the duodenoscope 10. And as explained above with respect to FIG. 1, various instruments (e.g., the catheter 14) are advanced from the elevator channel 18. Accordingly, the clip 130 and the cavity 133 can be configured such that the axis UA defining the center of the field of view of the transducer lens 114 laterally aligns with the elevator channel 18 axis EA rather than the center axis CA of the duodenoscope 10. Laterally aligning the axis UA with the elevator channel 18 axis EA can ensure that the ultrasonic image captured by the ultrasonic transducer 110 is centered on the various instruments advanced from the duodenoscope 10, ensuring that the various instruments can be seen.

Referring again to FIGS. 3A-3D, and primarily to FIG. 3A, the sleeve 140 is configured to slide around the distal end 12 of the duodenoscope 10. The sleeve 140 can include a protrusion 142 that extends into the elevator channel 18 as the sleeve 140 is slid over the duodenoscope 10. The protrusion 142 is configured to axially and rotationally position the sleeve 140 with respect to the distal end 12 of the duodenoscope 10. For example, the protrusion 142 can be used to determine how far along the distal end 12 of the duodenoscope 10 the sleeve 140 should be slid based on when the protrusion 142 contacts the proximal edge of the elevator channel 18 (as shown in FIG. 3A) and/or the distal edge of the elevator channel 18 (not shown). Likewise, by ensuring that the protrusion 142 extends into the elevator channel 18, the protrusion 142 can be used to determine the rotational positioning of the sleeve about the distal end 12 of the duodenoscope 10.

In some aspects, the protrusion 142 can be configured to be removed from the sleeve 140 once the sleeve 140 is positioned on the duodenoscope 10. For example, the protrusion 142 can include a breakaway feature 143 that allows the protrusion to be broken off of the sleeve 140. Removing the protrusion 142 can ensure that instruments (e.g., the catheter 14) are able to be extended from the duodenoscope 10 without being obstructed by the sleeve 140. In other aspects, the protrusion 142 can be formed from a flexible material that can be pushed out of the way by the various instruments (e.g., the catheter 14) that are extended from the duodenoscope 10. The protrusion 142 can be the same material as the sleeve 140 or a different material. For example, as explained more below, the protrusion 142 may be formed from the same elastomeric material as the sleeve 140. As another example, the protrusion 142 may be formed from a rigid plastic material.

The sleeve 140 can be configured to axially and rotationally position the clip 130 with respect to the duodenoscope 10. For example, the sleeve 140 can include one or more tab(s) 144 that extend radially from the sleeve 140. Further, the clip 130 can include one or more opening(s) 134 that correspond to the tab(s) 144. By ensuring the tab(s) 144 protrude through the opening(s) 134 as the clip 130 is placed over the distal end 12 of the duodenoscope 10 and the sleeve 140, the tab(s) 144 and the opening(s) 134 can be used to axially and rotationally position the clip 130 with respect to the sleeve 140. And, as explained above, the sleeve 140 can be axially and rotationally positioned using the protrusion 142.

In some aspects, the clip 130 includes a hinge configured to secure the clip 130 and the ultrasonic transducer 110 to the distal end 12 of the duodenoscope 10. For example, as best shown in the non-limiting aspect of FIG. 3A, the clip 130 has a hinge 132 that includes a knuckle and pin configuration 138. As another example, as shown in the non-limiting aspect of FIG. 13, the hinge 132 can include a dowel-pin hinge. However, according to other non-limiting aspects, the hinge 132 can alternately include a living hinge configuration 138. After the sleeve 140, the clip 130, and the ultrasonic transducer 110 are positioned over the distal end 12 of the duodenoscope 10, the hinge 132 can be closed around the duodenoscope 10 to secure the ultrasonic attachment assembly 100 in place. This can ensure that the ultrasonic attachment assembly 100 does not become dislodged or misaligned during an endoscopic procedure.

Figure 3B:
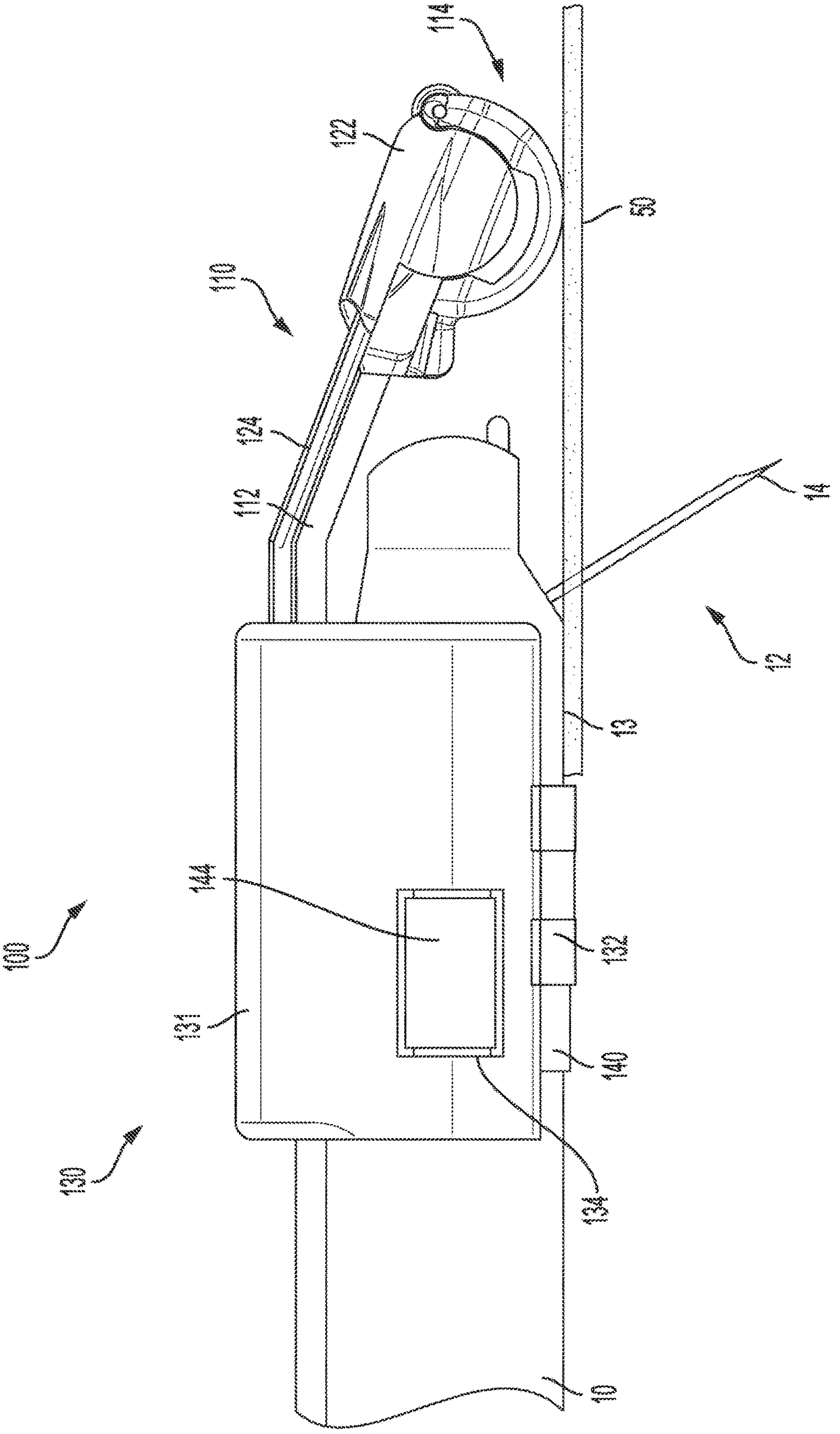
FIG. 3B illustrates a side view of the ultrasonic attachment assembly of FIG. 3A, according to at least one non-limiting aspect of this disclosure.
Figure 3D:
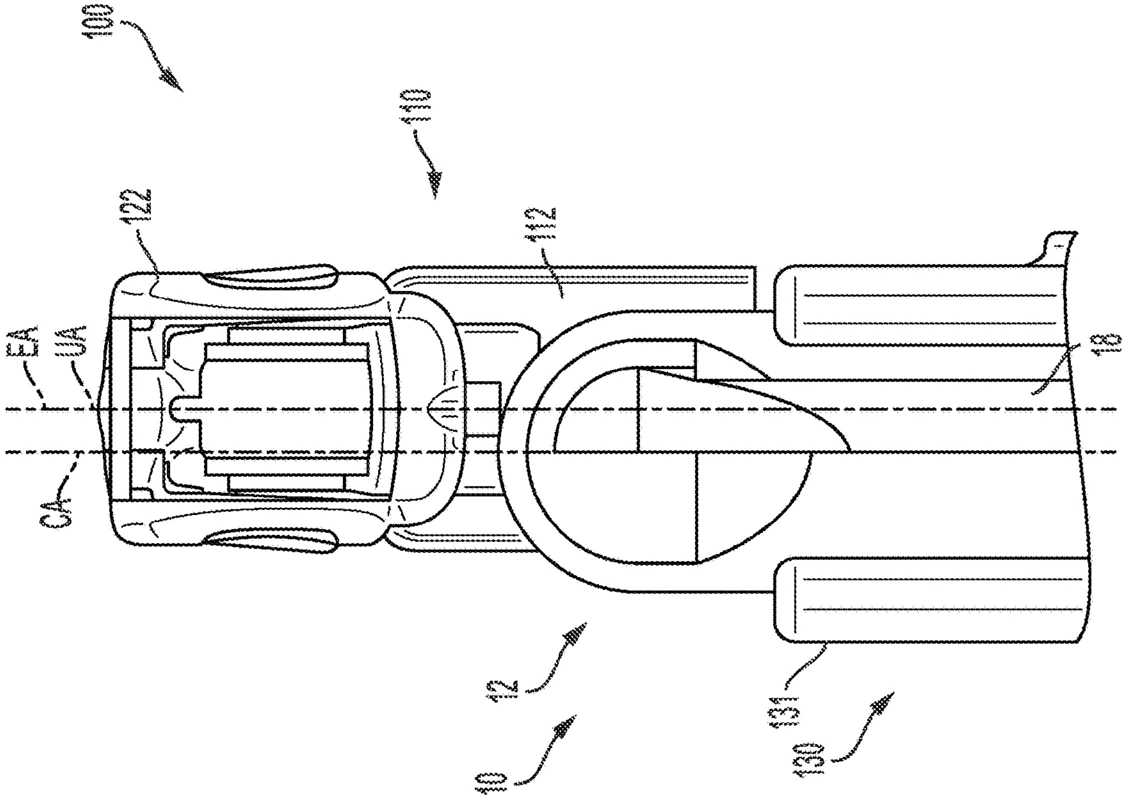
FIG. 3D illustrates a detailed bottom view of the ultrasonic assembly of FIG. 3A, according to at least one non-limiting aspect of this disclosure.
Figure 3C:
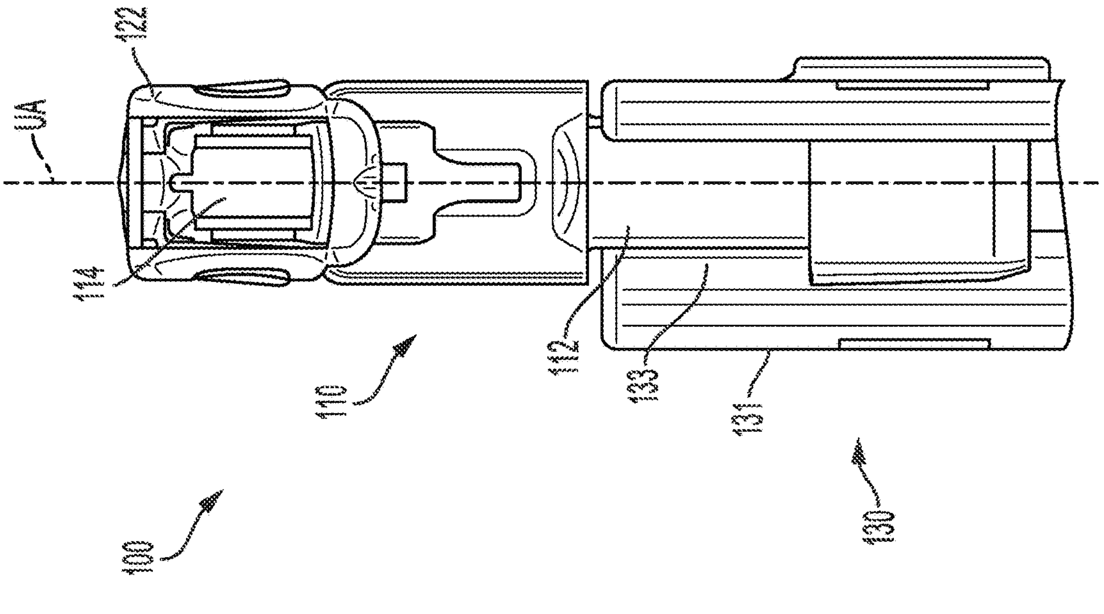
FIG. 3C illustrates a bottom view of the ultrasonic assembly of FIG. 3A without the duodenoscope, according to at least one non-limiting aspect of this disclosure.

Referring now primarily to FIG. 3B, the ultrasonic attachment assembly 100 can include a spine 124 and a lens cap 122. The spine 124 can be configured to position (e.g., bend and/or support) the transducer body 112 such that the transducer lens 114 is positioned to contact and acoustically couple with patient tissue 50 during a procedure. For example, the duodenoscope 10 can include a front face 13 (e.g., the side of the distal end 12 of the duodenoscope 10 that includes the elevator channel 18 and camera 24). The front face 13 can define a front face plane. The spine 124 can be configured to bend the elastomeric material of the transducer body 112 such that the transducer lens 114 is positioned substantially along the front face plane. Thus, maneuvering the front face 13 of the distal end 12 of the duodenoscope 10 to be proximate to and/or in contact with patient tissue 50 may also cause the transducer lens 114 to be in contact with the patient tissue 50, thereby acoustically coupling the transducer lens 114 with the patient tissue 50.

In some aspects, acoustic coupling between the transducer lens 114 and the patient tissue 50 requires that the transducer lens 114 be pressed against the patient tissue 50 with a minimum force. Thus, the transducer body 112 and/or the spine 124 can be constructed from a material (e.g., at least some of the elastomeric materials, rigid plastic materials, and/or rubber materials described herein) with enough stiffness to enable the transducer lens 114 to be pressed against the patient tissue 50 with the minimum force required for acoustic coupling. For example, the transducer body 112 and/or the spine 124 may be configured with enough elasticity to allow some movement of the transducer lens 114 relative to the distal end 12 of the duodenoscope 10 when the transducer lens 114 is pressed against patient tissue 50 but not so much movement that the force required for acoustic coupling cannot be achieved.

In some aspects, the lens cap 122 can be configured to protect the transducer lense 114 and/or provide mechanical support to the transducer lens 114 and/or spine 124.

In the non-limiting aspect of FIGS. 3A-3D, the clip body 131, the spine 124, and/or the lens cap 122 can be constructed from a rigid plastic material. For example, the clip body 131, the spine 124, and/or the lens cap 122 may be constructed from a rigid plastic material configured to resist elastic deformation. In some aspects, the clip body 131, the spine 124, and/or the lens cap 122 may be constructed from the same rigid plastic material. In other aspects, the clip body 131, the spine 124, and/or the lens cap 122 may be constructed from different rigid plastic materials. In some non-limiting aspects, the rigid plastic material can include at least one of acrylonitrile butadiene styrene (ABS), polypropylene, polycarbonate, polyetherimide (PEI).

The rigid plastic material can be characterized as having a relatively high rigidity, such as a Shore A Durometer at the higher end of the aforementioned range (e.g., greater than or equal to OA and less than or equal to 100A). For example, according to some non-limiting aspects, it may be desirable to enhance an acoustic coupling of the transducer lens 114, which can be accomplished with a relatively high rigidity (e.g., approximately 100A). However, according to other non-limiting aspects, maintaining a degree of flexibility may be desirable to promote patient comfort and safety while preserving a certain degree of acoustic coupling. As such, configuring the transducer body 112 to a predetermined elastic rigidity within a "cross-over" zone (e.g., greater than or equal to 90A and less than or equal to 100A) could be preferable. This can be particularly important, especially in non-limiting aspects wherein an offset between a central axis of the duodenoscope and elevator channel axis, as will be described in further detail herein, requires that a dimension of the clip 130 and/or ultrasonic transducer 110 transcend a critical dimension (e.g., width) of the duodenoscope. For example, according to some non-limiting aspects, the critical dimension of the duodenoscope can be defined based on an outer diameter of the duodenoscope. In other words, the predetermined elastic rigidity within the "cross-over" zone can be particularly configured to optimize instrument visibility provided by the offset, acoustic coupling of the transducer lens 114, and patient comfort as the duodenoscope traverses various orifices of the patient's body.

In the non-limiting aspect of FIGS. 3A-3D, the sleeve 140 can be constructed from an elastomeric material (e.g., an elastic polymer), such as the elastomeric materials described above. For example, the sleeve 140 may be constructed from an elastomeric material that enables the sleeve 140 to be stretched over the distal end 12 of the duodenoscope 10 to hold the sleeve 140 securely in place without the need for the hinge 132. In some aspects, the sleeve 140 may be constructed from the same elastomeric material as the transducer body 112. In other aspects, the sleeve 140 and the transducer body 112 may be constructed from different elastomeric materials.

Figure 4A:
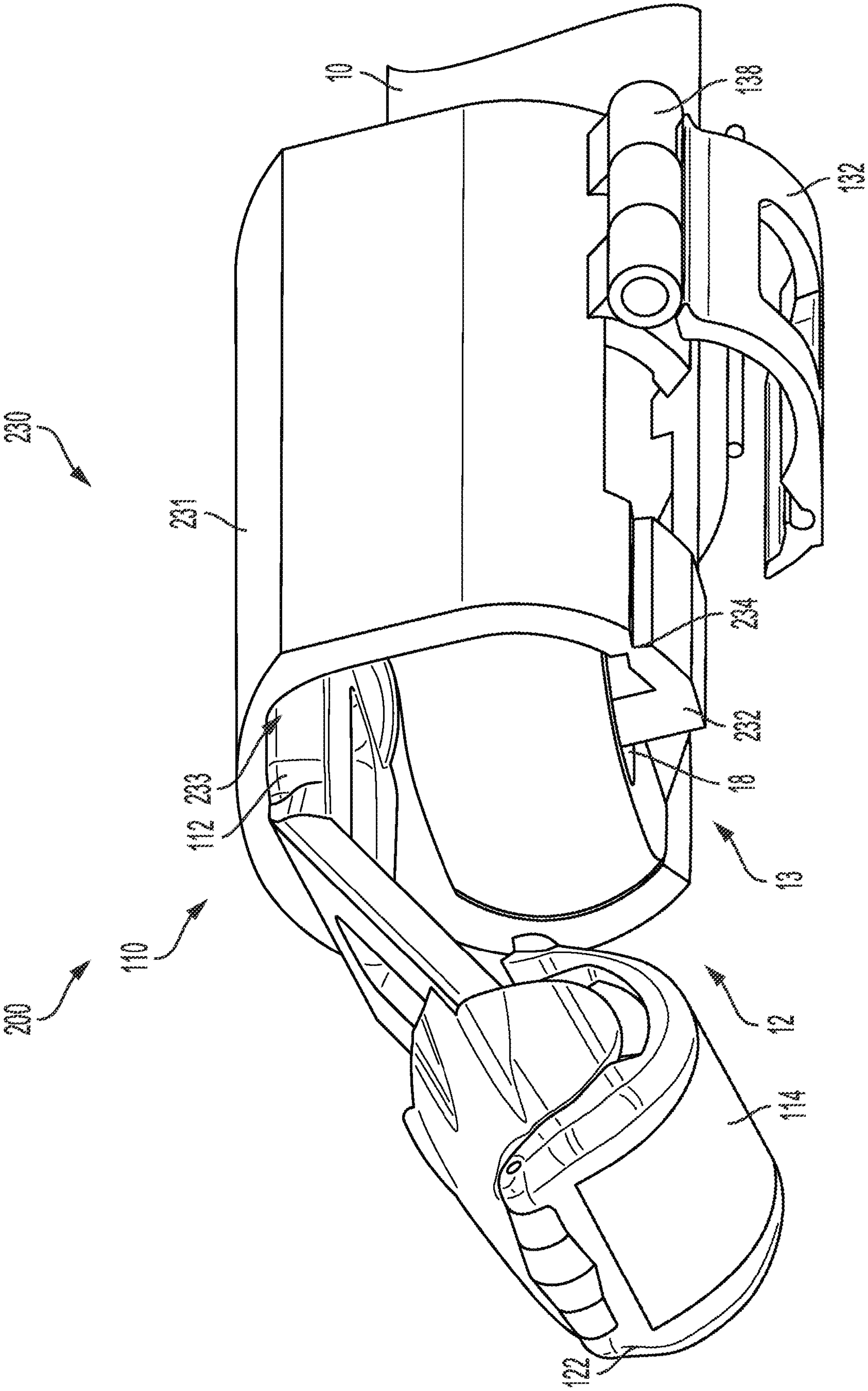
FIG. 4A illustrates a perspective view of an ultrasonic attachment assembly positioned on the distal end of a duodenoscope, according to at least one non-limiting aspect of this disclosure.
Figure 4B:
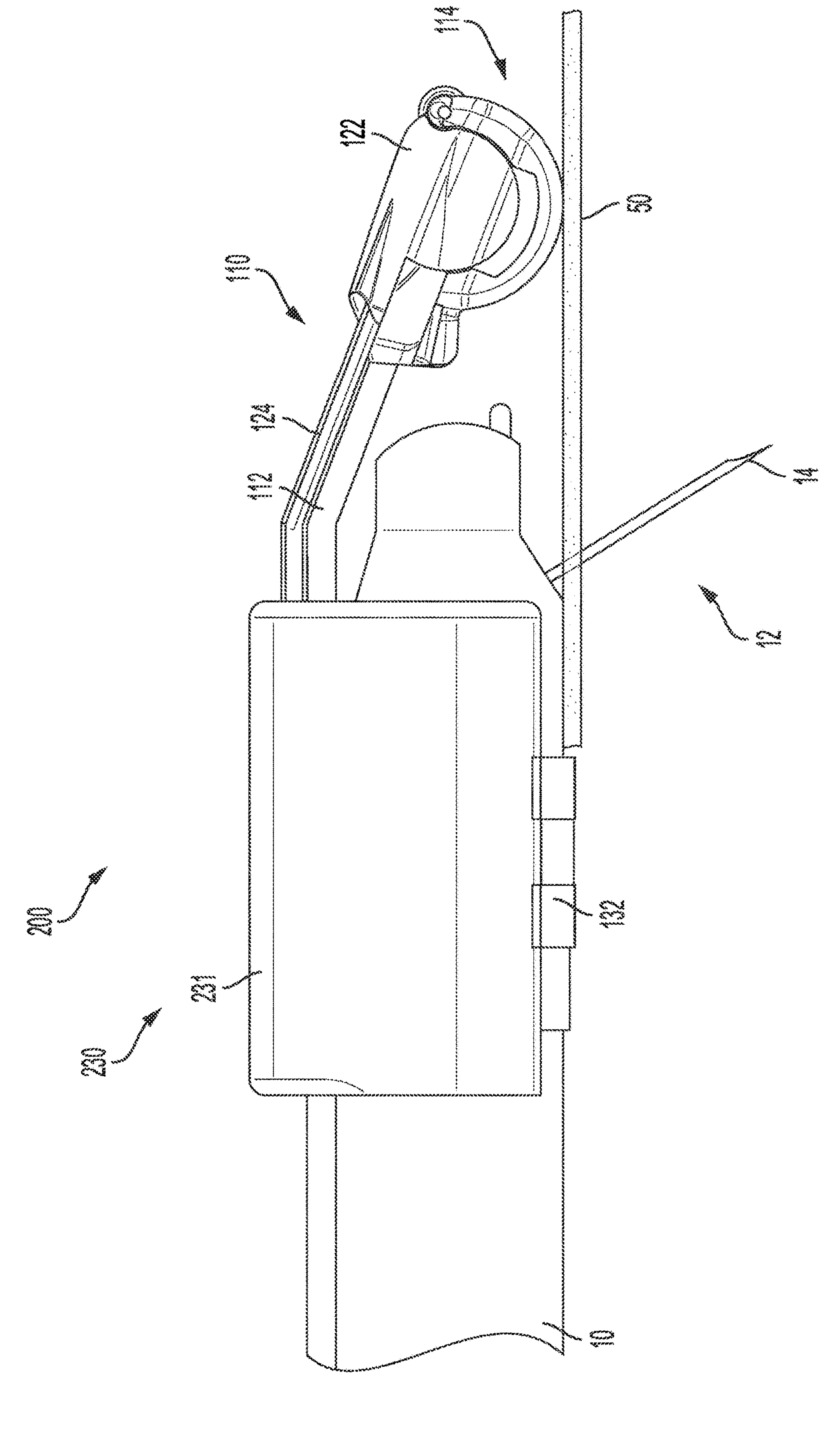
FIG. 4B illustrates a side view of the ultrasonic attachment assembly of FIG. 4A, according to at least one non-limiting aspect of this disclosure.

Referring now to FIGS. 4A-4B, an ultrasonic attachment assembly 200 is shown positioned on the distal end 12 of the duodenoscope 10. Similar to the ultrasonic attachment assembly 100 above, the ultrasonic assembly 200 includes the ultrasonic transducer 110 and a clip 230. The clip 230 is similar in many respects to the clip 130. For example, the clip 230 includes a clip body 231 that can be similar to the clip body 131 and a cavity 233 that can be similar to the cavity 133.

The ultrasonic attachment assembly 200 may not include a sleeve, such as the sleeve 140 of FIGS. 3A-3D. In this aspect, the clip 230 can be placed directly over the distal end 12 of the duodenoscope 10 without the use of a sleeve. The clip 230 can include a protrusion 232 that has a similar function to the protrusion 142 of the sleeve 140. For example, the protrusion 232 can be configured to extend into the elevator channel 18 as the clip 230 is placed over the distal end 12 of the duodenoscope 10. The protrusion 232 is configured to axially and rotationally position clip 230 with respect to the distal end 12 of the duodenoscope 10. For example, the protrusion 232 can be used to determine how far along the distal end 12 of the duodenoscope 10 to position the clip 230 based on when the protrusion 232 contacts the proximal edge and/or the distal edge of the elevator channel 18. Likewise, the protrusion 232 can be used to rotationally position the clip 230 around the distal end 12 of the duodenoscope 10 by ensuring that the protrusion 232 extends into the elevator channel 18.

The protrusion 232 can be configured to be removed from the clip 230 once the clip 230 is positioned on the duodenoscope 10. For example, the protrusion 232 can include a breakaway feature 234 that allows the protrusion to be broken off of the clip 230. Removing the protrusion 232 can ensure that instruments (e.g., catheter 14) are able to extend from the duodenoscope 10 elevator channel 18 without being obstructed by the clip 230.

Figure 5:
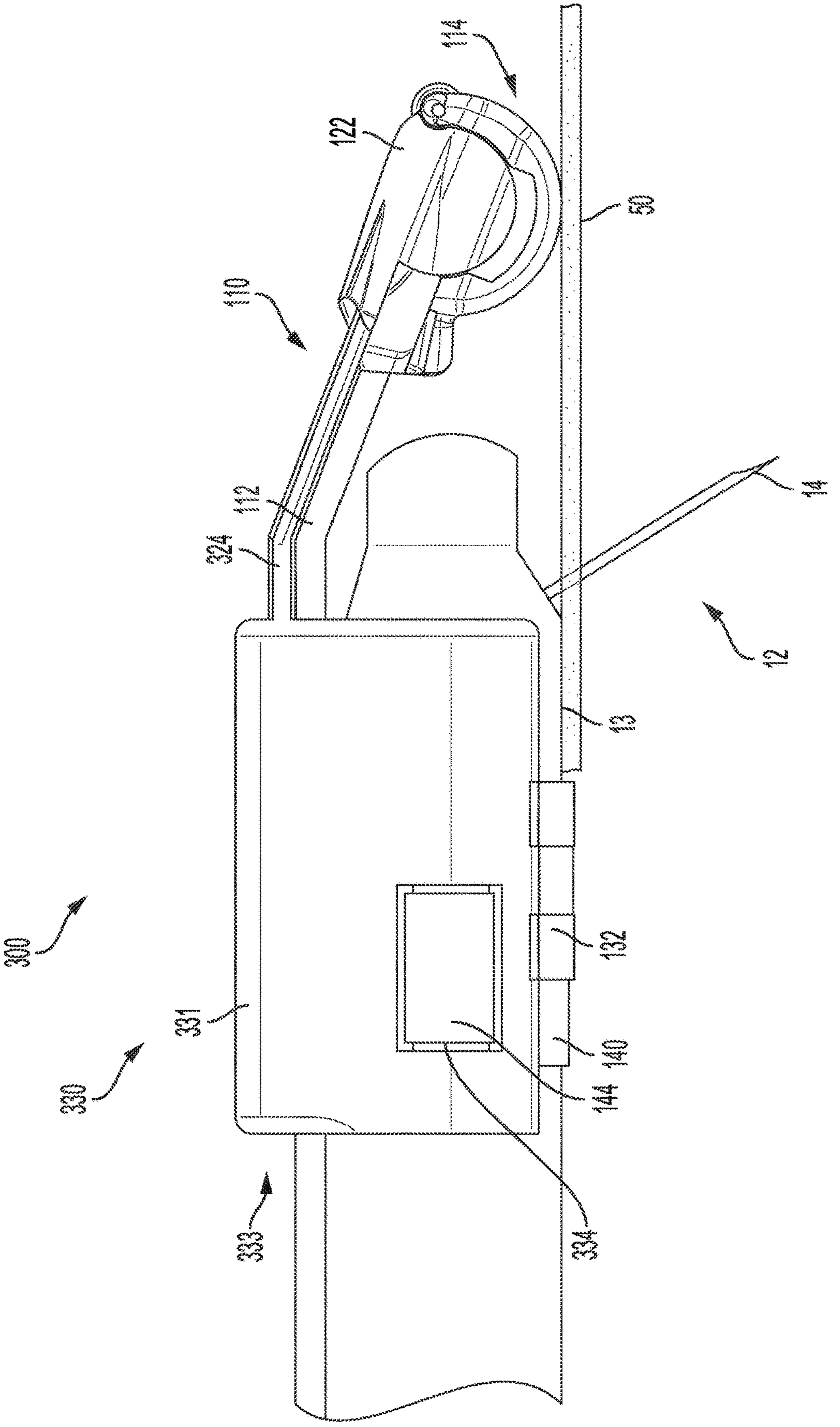
FIG. 5 illustrates a side view of an ultrasonic attachment assembly positioned on the distal end of a duodenoscope, according to at least one non-limiting aspect of this disclosure.

Referring now to FIG. 5, an ultrasonic attachment assembly 300 is shown positioned on the distal end 12 of the duodenoscope 10. Similar to the ultrasonic attachment assemblies 100 and 200 above, the ultrasonic attachment assembly 300 includes the ultrasonic transducer 110, a clip 330, and a spine 324.

In the non-limiting aspect of FIG. 5, the clip 330 and the spine 324 are formed as a single piece. Further, the clip 330 and the spine 324 may be constructed from the same rigid plastic material, such as one of the rigid plastic materials described herein. The spine 324 can be similar in many respects to the spine 124 described above with respect to ultrasonic attachment assembly 100. For example, the spine 324 can be configured to position the transducer lens 114 substantially along the same plane as the front face 13 of the distal end 12 of the duodenoscope 10 to enable acoustic coupling between the transducer lens 114 and patient tissue 50.

In some aspects, the clip 330 is similar to the clip 130. For example, the clip 330 includes a clip body 331 that can be similar to the clip body 131, a cavity 333 that can be similar to the cavity 133, and one or more opening(s) 334 that can be similar to the opening(s) 134. Furthermore, the ultrasonic attachment assembly 300 can include the sleeve 140 (as described above) for axially and rotationally positioning the clip 330 with respect to the distal end 12 of the duodenoscope 10.

In other aspects, the clip 330 can be similar to the clip 230. For example, the clip 330 may be placed directly over the distal end 12 of the duodenoscope 10 without the use of a sleeve for positioning (e.g., the sleeve 140 may not be included in the ultrasonic attachment assembly 300). Further, the clip 330 can include a protrusion (not shown in FIG. 5) for axially and rotationally positioning the clip 330 with respect to the distal end 12 of the duodenoscope 10, similar to the protrusion 232 described above.

Figure 6A:
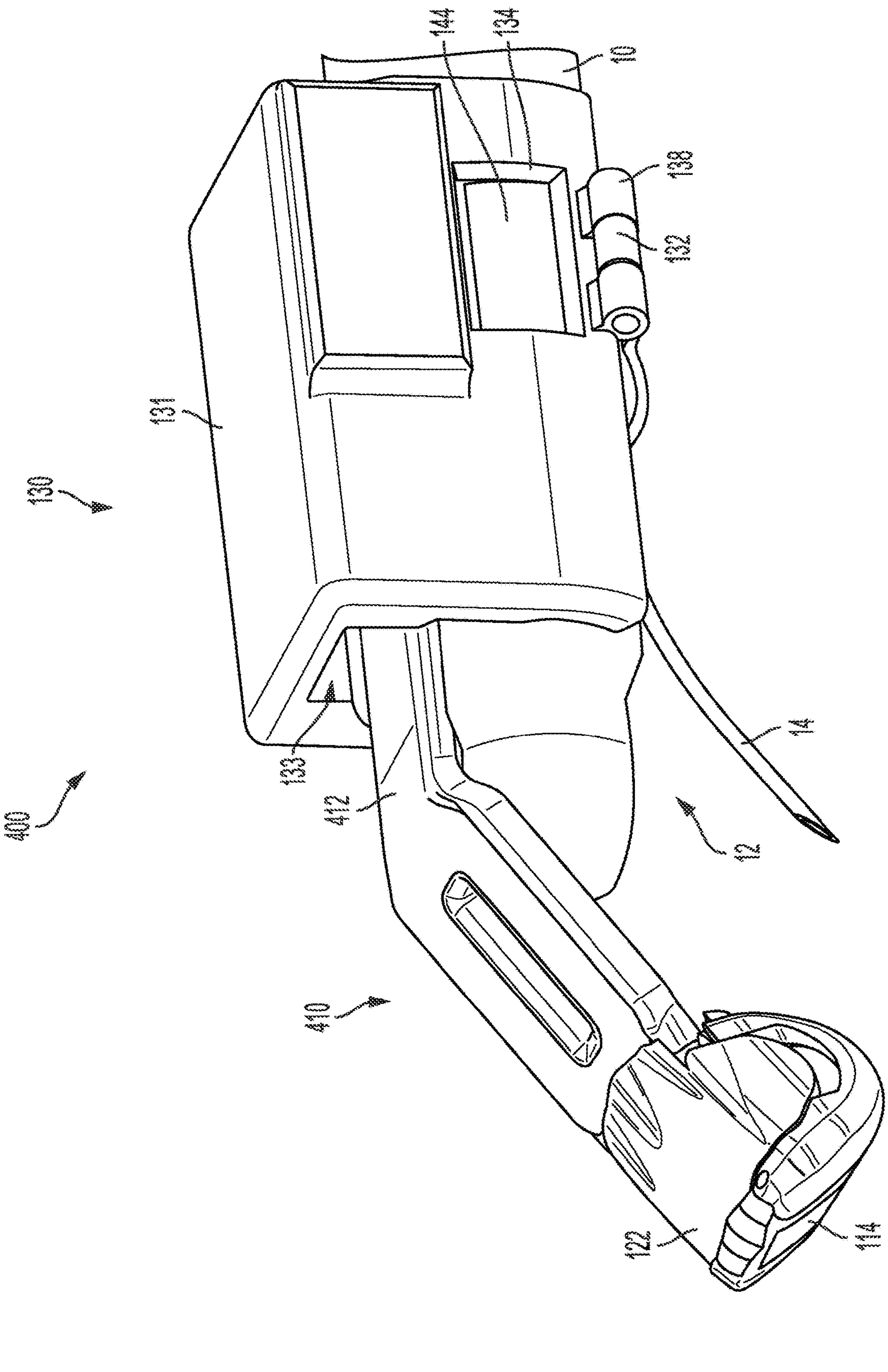
FIG. 6A illustrates a perspective view of an ultrasonic attachment assembly positioned on the distal end of a duodenoscope, according to at least one non-limiting aspect of this disclosure.
Figure 6B:
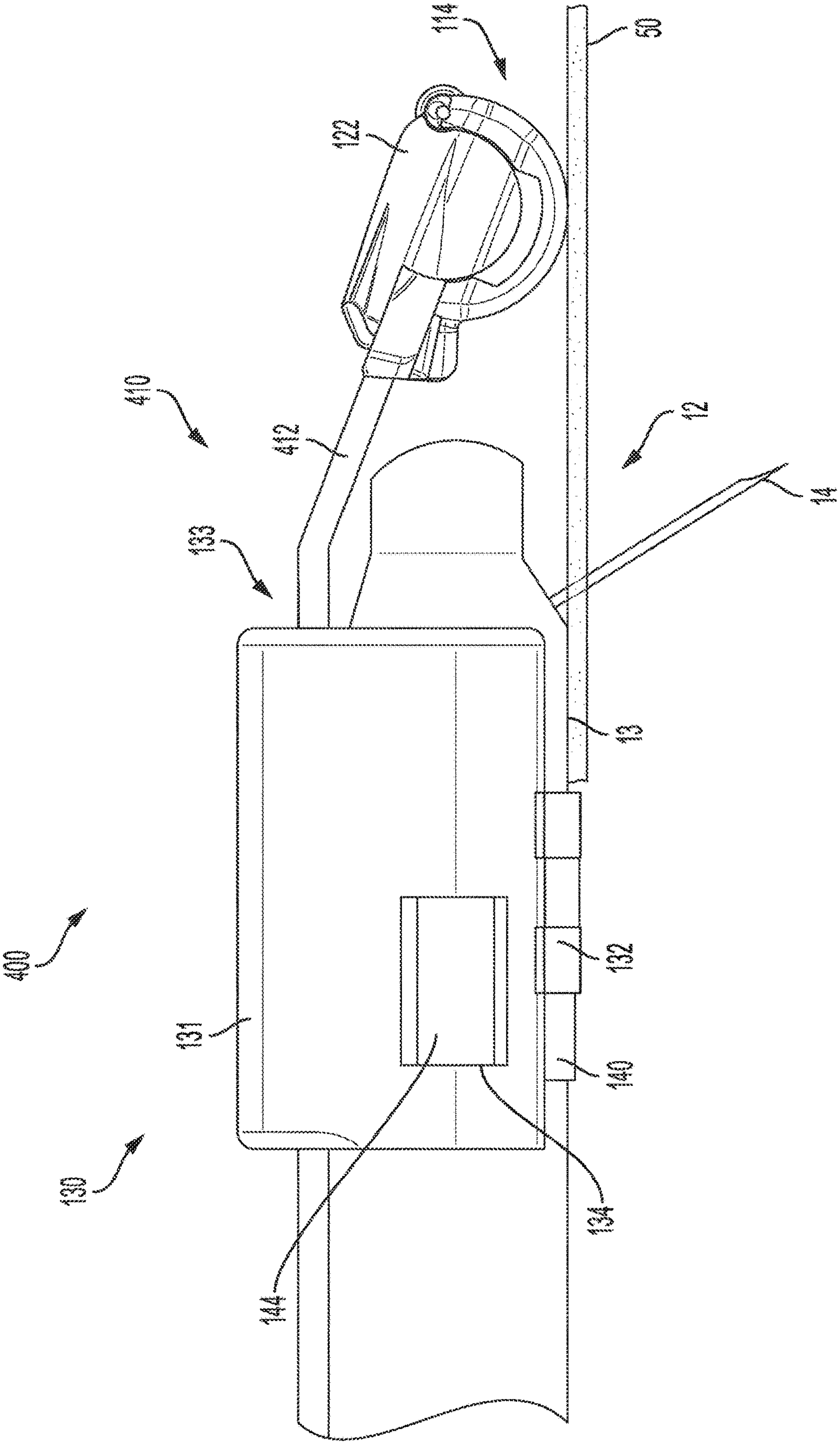
FIG. 6B illustrates a side view of the ultrasonic attachment assembly of FIG. 6A, according to at least one non-limiting aspect of this disclosure.

Referring now to FIGS. 6A-6B, an ultrasonic attachment assembly 400 is shown positioned on the distal end 12 of the duodenoscope 10. Similar to the ultrasonic attachment assembly 100, the ultrasonic assembly 400 includes an ultrasonic transducer 410, the clip 130, and the sleeve 140.

In the non-limiting aspect of FIG. 6A-6B, the ultrasonic transducer 410 can include a transducer body 412 and the transducer lens 114. The transducer body 412 can be formed from a rigid plastic material, such as one of the rigid plastic materials described herein. The transducer body 412 can be configured to position the transducer lens 114 substantially along the same plane as the front face 13 of the distal end 12 of the duodenoscope 10 to enable acoustic coupling between the transducer lens 114 and patient tissue 50. In some aspects, the rigid plastic material of the transducer body 412 can be formed to include a bend configured to position the transducer lens 114 substantially along the same plane as the front face 13 of the distal end 12 of the duodenoscope 10. Thus, the ultrasonic attachment assembly 400 may not include a rigid plastic spine, such as the spine 124 described above with respect to FIGS. 3A-3D. In some aspects, the transducer body 412 may be formed to include a curved surface that matches the outer diameter of the distal end 12 of the duodenoscope 10.

Figure 7:
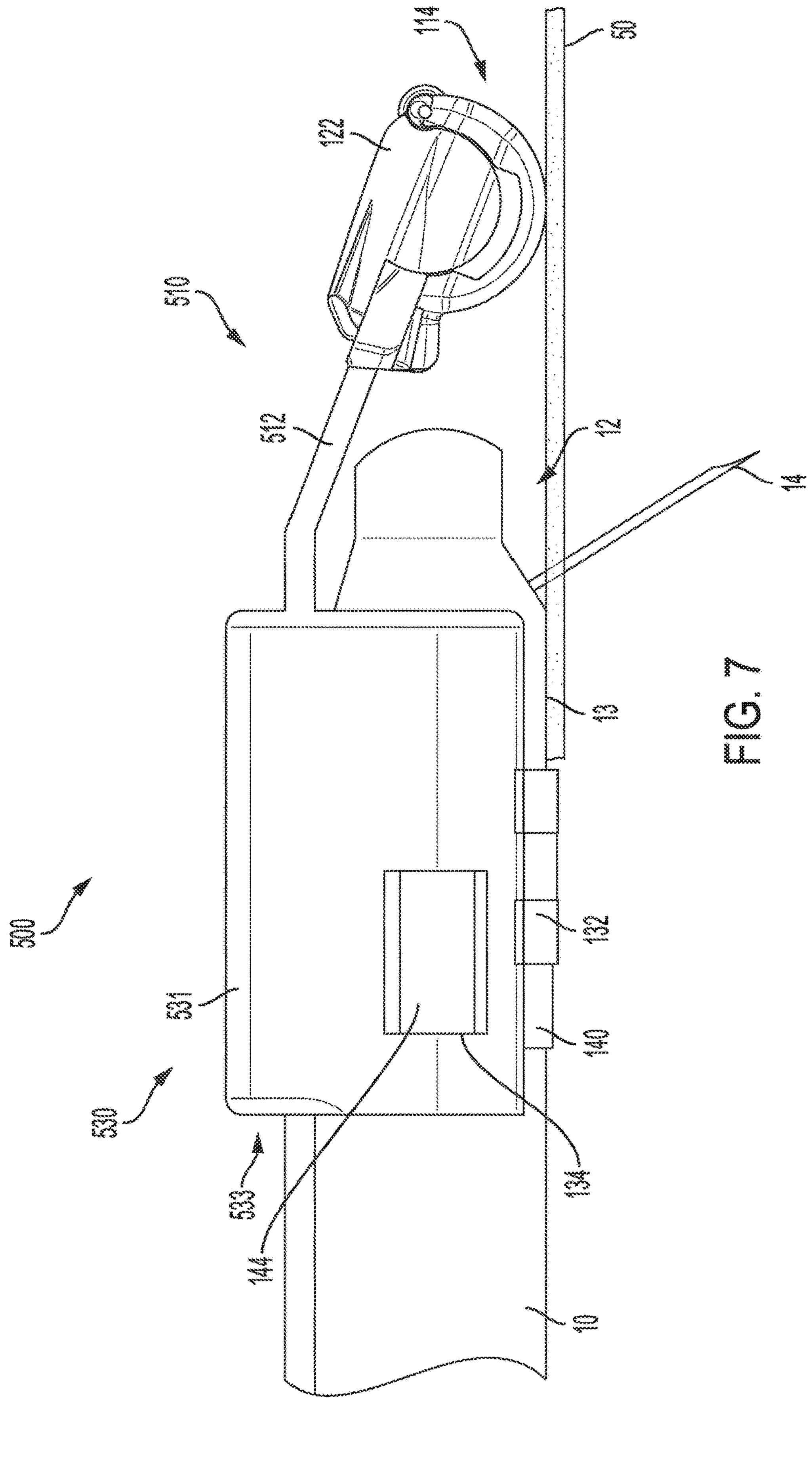
FIG. 7 illustrates a side view of an ultrasonic attachment assembly positioned on the distal end of a duodenoscope, according to at least one non-limiting aspect of this disclosure.

Referring now to FIG. 7, an ultrasonic attachment assembly 500 is shown positioned on the distal end 12 of the duodenoscope 10. Similar to the ultrasonic attachment assembly 400, the ultrasonic attachment assembly 500 includes an ultrasonic transducer 510, a clip 530, and the sleeve 140.

According to the non-limiting aspect of FIG. 7, the transducer body 512 and the clip 530 are formed as a single piece. Further, the transducer body 512 and the clip 530 may be constructed from the same rigid plastic material, such as one of the rigid plastic materials described herein.

The ultrasonic transducer 510 includes a transducer body 512 and the transducer lens 114. The ultrasonic transducer 510 can be similar in many respects to the ultrasonic transducer 410 described above with respect to FIGS. 6A-6B. For example, like the transducer body 412 described above, the transducer body 512 can be formed from a rigid plastic material and can be configured to position the transducer lens 114 substantially along the same plane as the front face 13 of the distal end 12 of the duodenoscope 10 to enable acoustic coupling between the transducer lens 114 and patient tissue 50.

The clip 530 includes a clip body 531 and a cavity 533. The clip 530 can be similar in many respects to the clip 130 described above with respect to FIGS. 3A-3D. For example, the clip body 531 can be similar to the clip body 131 and the cavity 533 can be similar to the cavity 133.

Figure 8A:
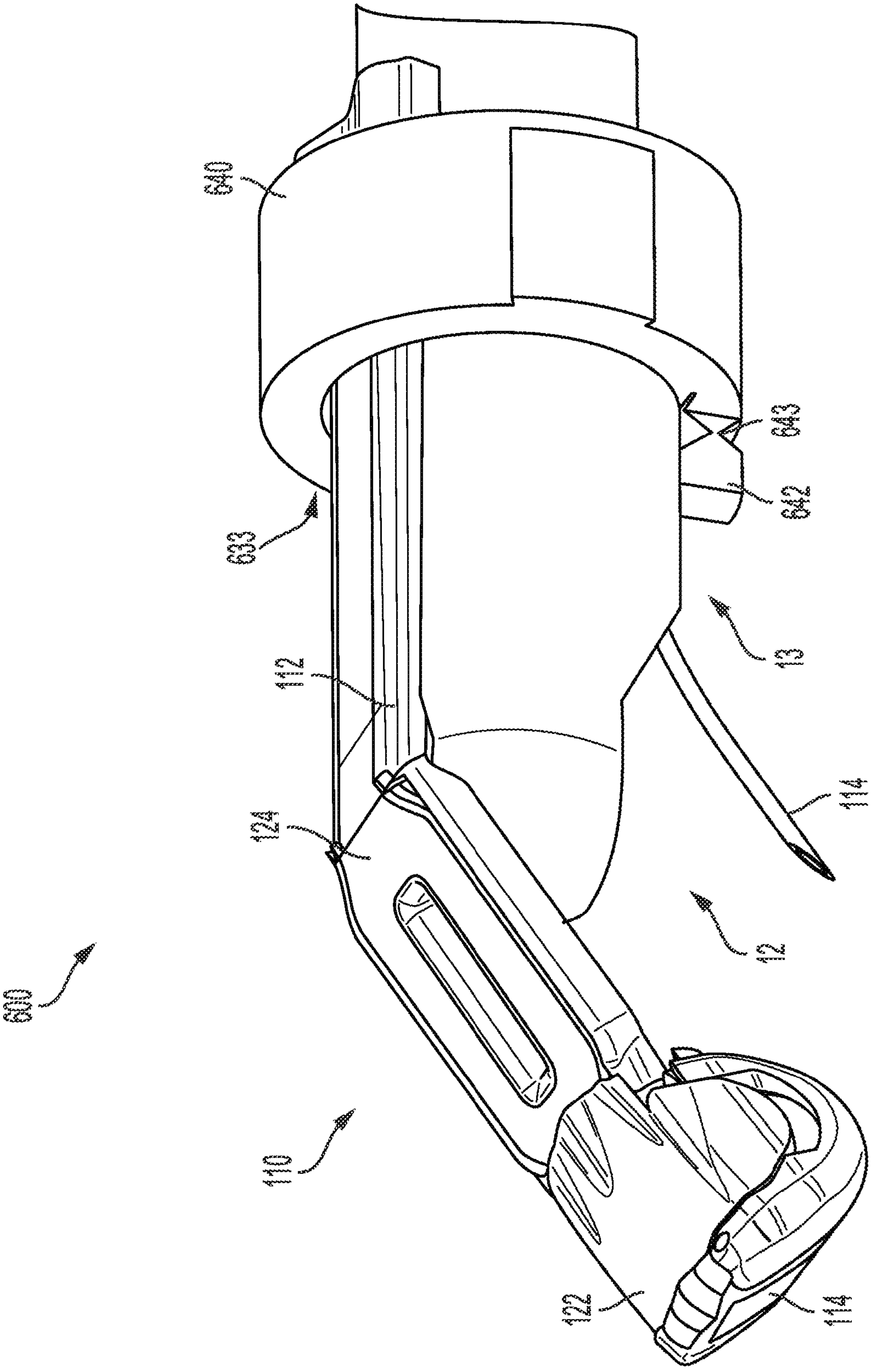
FIG. 8A illustrates a perspective view of an ultrasonic attachment assembly positioned on the distal end of a duodenoscope, according to at least one non-limiting aspect of this disclosure.
Figure 8B:
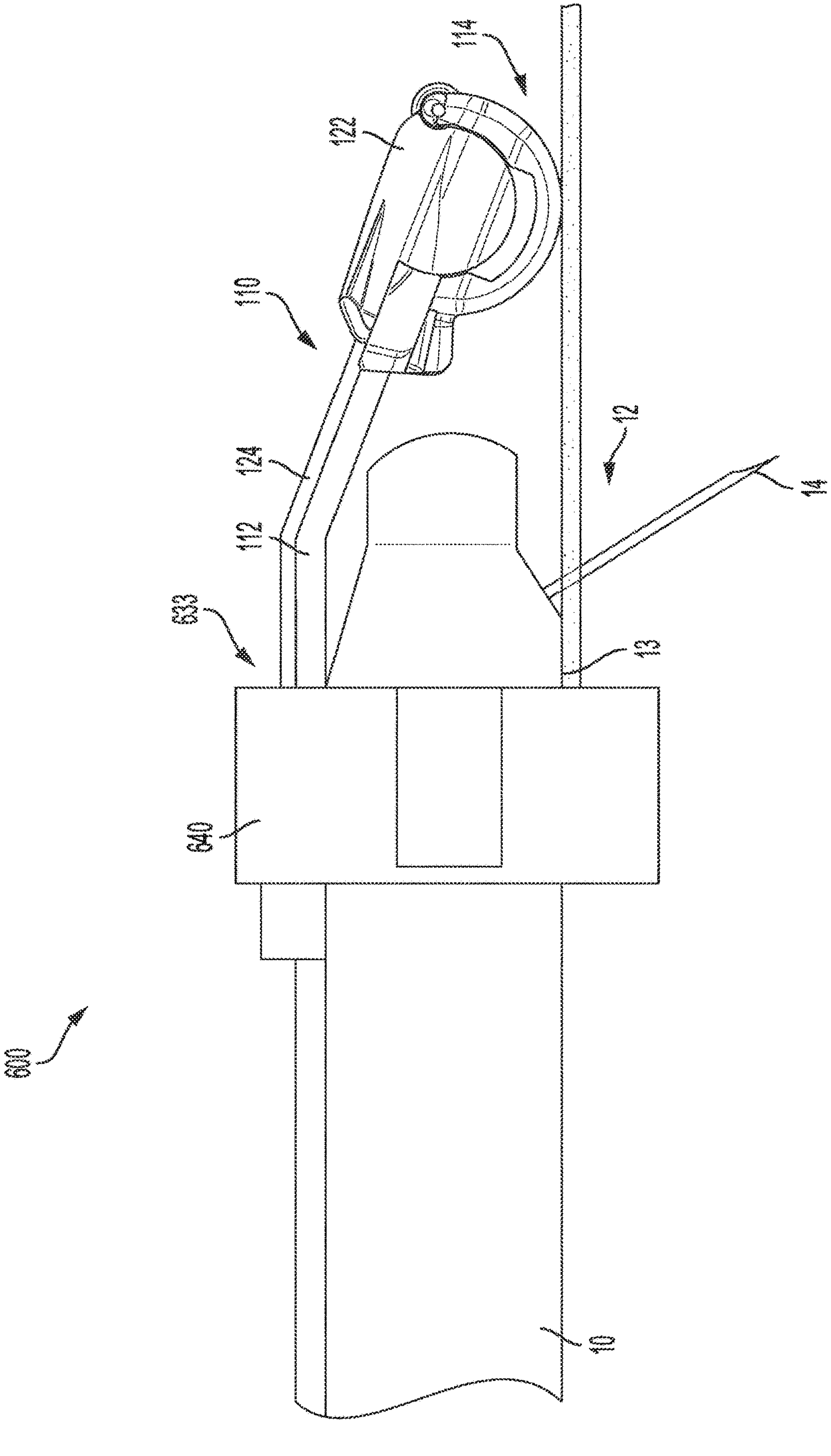
FIG. 8B illustrates a side view of the ultrasonic attachment assembly of FIG. 8A, according to at least one non-limiting aspect of this disclosure.

Referring now to FIGS. 8A-8B, an ultrasonic attachment assembly 600 is shown positioned on the distal end 12 of the duodenoscope 10. Similar to the ultrasonic attachment assembly 100 above, the ultrasonic attachment assembly 600 includes the ultrasonic transducer 110, the spine 124, and a sleeve 640.

The sleeve 640 is similar in many respects to the sleeve 140. For example, the sleeve 640 is configured to slide around the distal end 12 of the duodenoscope 10. The sleeve 640 can include a protrusion 642 that extends into the elevator channel 18 as the sleeve 640 is slid over the duodenoscope 10. The protrusion 642 is configured to axially and rotationally position the sleeve 640 with respect to the distal end 12 of the duodenoscope 10. For example, the protrusion 642 can be used to determine how far along the distal end 12 of the duodenoscope 10 the sleeve 640 should be slid based on when the protrusion contacts the proximal edge of the elevator channel 18 (as shown in FIG. 8A) and/or the distal edge of the elevator channel (not shown). Likewise, by ensuring that the protrusion 642 extends into the elevator channel 18, the protrusion 642 can be used to determine rotational positioning of the sleeve 640 about the distal end 12 of the duodenoscope 10.

The protrusion 642 can be configured to be removed from the sleeve 640 once the sleeve 640 is positioned on the duodenoscope 10. For example, the protrusion 642 can include a breakaway feature 643 that allows the protrusion to be broken off of the sleeve 640. Removing the protrusion 642 can ensure that instruments (e.g., the catheter 14) are able to be extended from the duodenoscope 10 without being obstructed by the sleeve 640. In other aspects, the protrusion 642 can be formed from a flexible material that can be pushed out of the way by the various instruments (e.g., the catheter 14) that are extended from the duodenoscope 10. The protrusion 642 can be the same material as the sleeve 640 or a different material. For example, as explained more below, the protrusion 642 may be formed from the same elastomeric material as the sleeve 640. As another example, the protrusion 642 may be formed from a rigid plastic material. Additionally, according to some non-limiting aspects, a single-piece construction of the sleeve 640 can combine a transducer housing and clip while creating a desired offset of axes to promote visibility and operability.

Still referring to FIGS. 8A-8B, in some aspects, the sleeve 640 can include features similar to the clip 130 described above with respect to FIGS. 3A-3D. For example, sleeve 640 can include a cavity 633 similar to the cavity 133 of the clip 130. The cavity 633 is configured to support transducer body 112. Accordingly, when the sleeve 640 is placed over the distal end 12 of the duodenoscope 10, the cavity 633 can hold the transducer body 112 such that the transducer lens 114 is positioned distally with respect to the distal end 12 of the duodenoscope 10.

Also similar to the clip 130 and the cavity 133 described above with respect to FIGS. 3A-3D, the sleeve 640 and the cavity 633 can be configured to laterally position the transducer lens 114 with respect to the duodenoscope 10. As explained above with respect to FIG. 3D, the elevator channel 18 axis EA is offset from the center axis CA of the duodenoscope 10. The sleeve 640 and the cavity 633 can be configured such that the axis UA (not shown in FIGS. 8A-8B) defining the center of the field of view of the transducer lens 114 laterally aligns with the elevator channel 18 axis EA rather than the center axis CA of the duodenoscope 10. Laterally aligning the axis UA with the elevator channel 18 axis EA can ensure that the ultrasonic image captured by the ultrasonic transducer 110 is centered on the various instruments advanced from the duodenoscope 10.

Still referring to FIGS. 8A-8B, the sleeve 640 can be constructed from an elastomeric material (e.g., an elastic polymer), such as the elastomeric materials described above. In some aspects, the elastomeric material of the sleeve 640 may be a rubber material and may configured to have a high durometer to provide stuffiness for securing the sleeve 640 to the duodenoscope 10 and/or for supporting the ultrasonic transducer 110. A high durometer may be characterized as a durometer no less than 40, such as no less than 50, 60, 70, 80, or no less than 90. In some aspects, high durometer materials may be used for the sleeve, the spine, and/or the transducer body, including silicone, fluoroelastomers, and ethylene propylene, amongst others.

For example, the sleeve 640 may be constructed from an elastomeric material that enables the sleeve 640 to be stretched over the distal end 12 of the duodenoscope 10 to hold the sleeve 640 and the ultrasonic transducer 110 securely in place without the need for a clip or a clasp, such as the clip 130 and the hinge 132 described above. In some aspects, the sleeve 640 may be constructed from the same elastomeric material as the transducer body 112. In other aspects, the sleeve 640 and the transducer body 112 may be constructed from different elastomeric materials. Furthermore, in some aspects the sleeve 640 and the transducer body 112 may be formed as a single piece. In other aspects, the sleeve 640 and the transducer body 112 may be two separate pieces.

Figure 9:
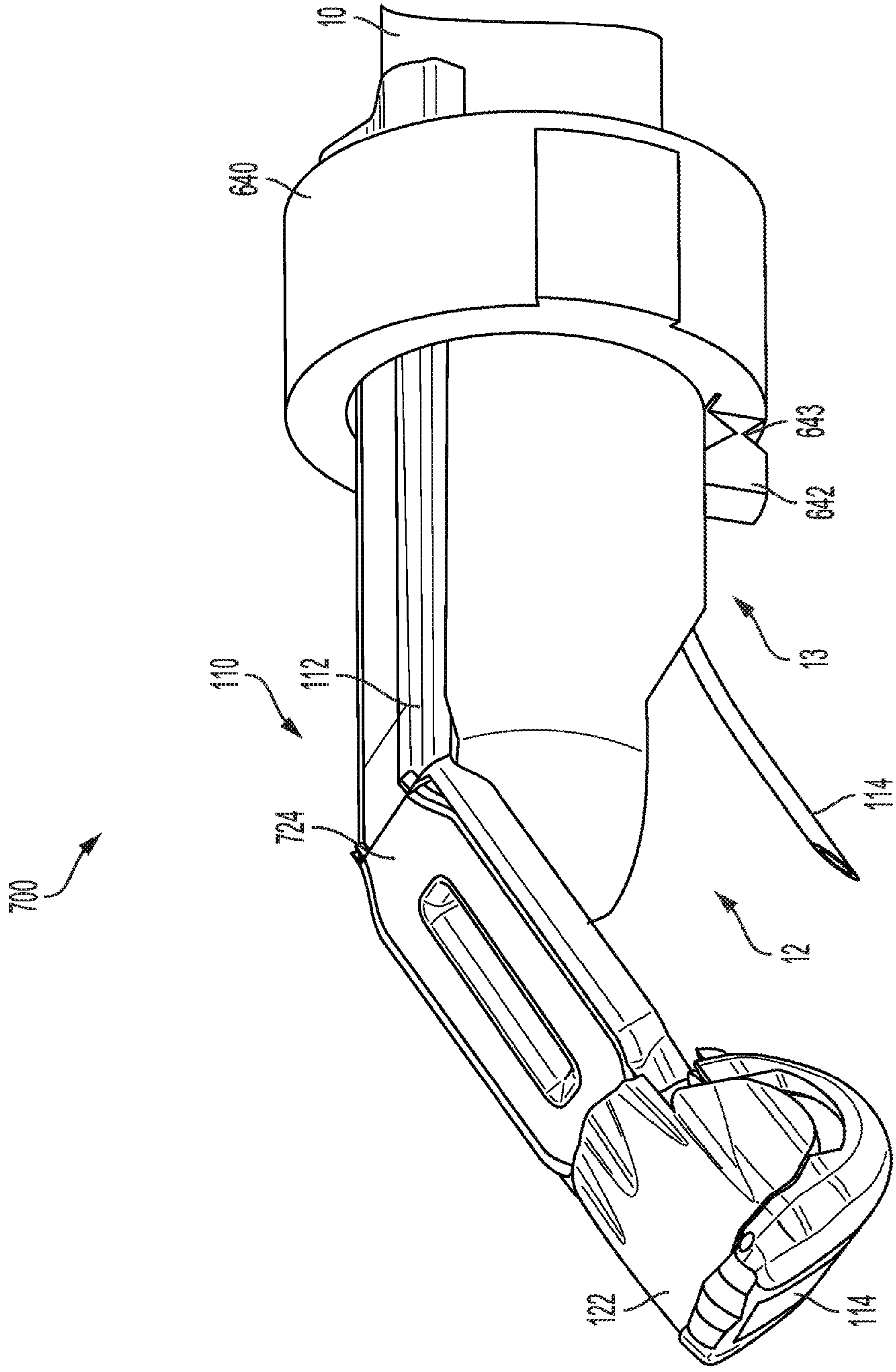
FIG. 9 illustrates a perspective view of an ultrasonic attachment assembly positioned on the distal end of a duodenoscope, according to at least one non-limiting aspect of this disclosure.

Referring now to FIG. 9, an ultrasonic attachment assembly 700 is shown positioned on the distal end 12 of the duodenoscope 10. Similar to the ultrasonic attachment assembly 600 above, the ultrasonic attachment assembly 700 includes the ultrasonic transducer 110, the sleeve 640, and a spine 724.

The spine 724 can be similar in many respects to the spine 124 described above with respect to FIGS. 3A-3D. In the non-limiting aspect of FIG. 9, the spine 724 is constructed from an elastomeric material having a high durometer, such as the elastomeric material having a high durometer described above. Accordingly, the spine 724 can be configured to position (e.g., bend and/or support) the transducer body 112 such that the transducer lens 114 is positioned to contact and acoustically couple with patient tissue 50 during a procedure. For example, the spine 724 can be configured to bend the elastomeric material of the transducer body 112 such that the transducer lens 114 is positioned substantially along the front face plane defined by the front face 13 of the distal end 12 of the transducer 10.

In some aspects, the spine 724, the transducer body 112, and/or the sleeve 640 can be constructed from the same elastomeric material having a high durometer. In other aspects, the spine 724, the transducer body 112, and/or the sleeve 640 can be constructed from different elastomeric materials each having a high durometer. In one aspect, the spine 724 and the transducer body 112 can be formed as a single piece. In another aspect, the spine 724 and the sleeve 640 can be formed as a single piece. In yet another aspect, the spine 724 and the transducer body 112 can be formed as a single piece. And in yet another aspect, the spine 724, the transducer body 112, and the sleeve 640 can be formed as a single piece.

Figure 10:
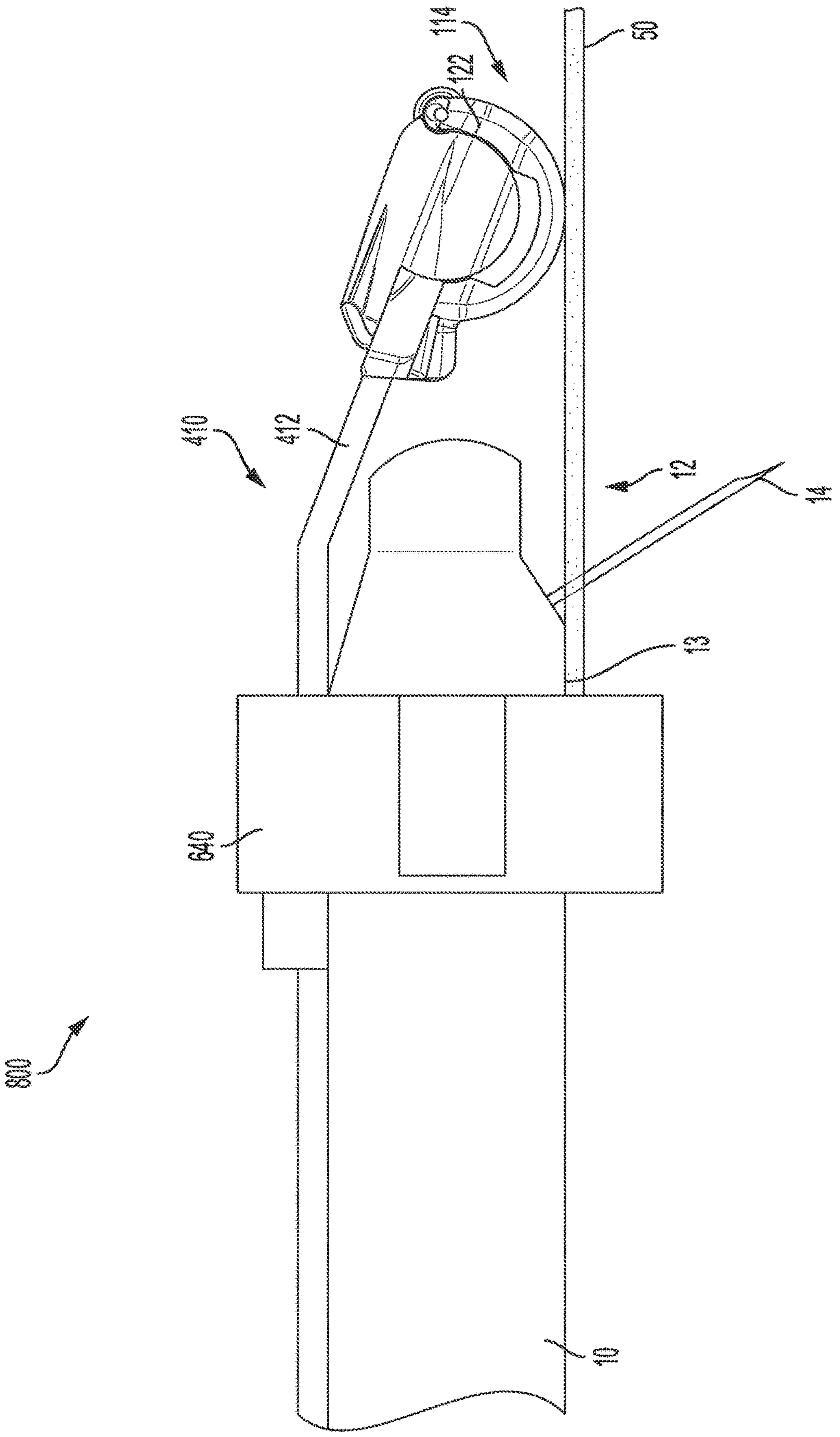
FIG. 10 illustrates a side view of an ultrasonic attachment assembly positioned on the distal end of a duodenoscope, according to at least one non-limiting aspect of this disclosure.

Referring now to FIG. 10, an ultrasonic attachment assembly 800 is shown positioned on the distal end 12 of the duodenoscope 10. The ultrasonic assembly 800 includes the sleeve 640 described above with respect to FIGS. 8A-8B and the ultrasonic transducer 410 described above with respect to FIGS. 6A-6B.

As explained above, the transducer body 412 can be formed from a rigid plastic material, such as one of the rigid plastic materials described herein. The transducer body 412 can be configured to position the transducer lens 114 substantially along the same plane as the front face 13 of the distal end 12 of the duodenoscope 10 to enable acoustic coupling between the transducer lens 114 and patient tissue 50. In some aspects, the rigid plastic material of the transducer body 412 can be formed to include a bend configured to position the transducer lens 114 substantially along the same plane as the front face 13 of the distal end 12 of the duodenoscope 10. Thus, the ultrasonic attachment assembly 800 may not include a rigid plastic spine or an elastic spine with a high durometer, such as the spine 124 and the spine 724 described above.

Figure 11:
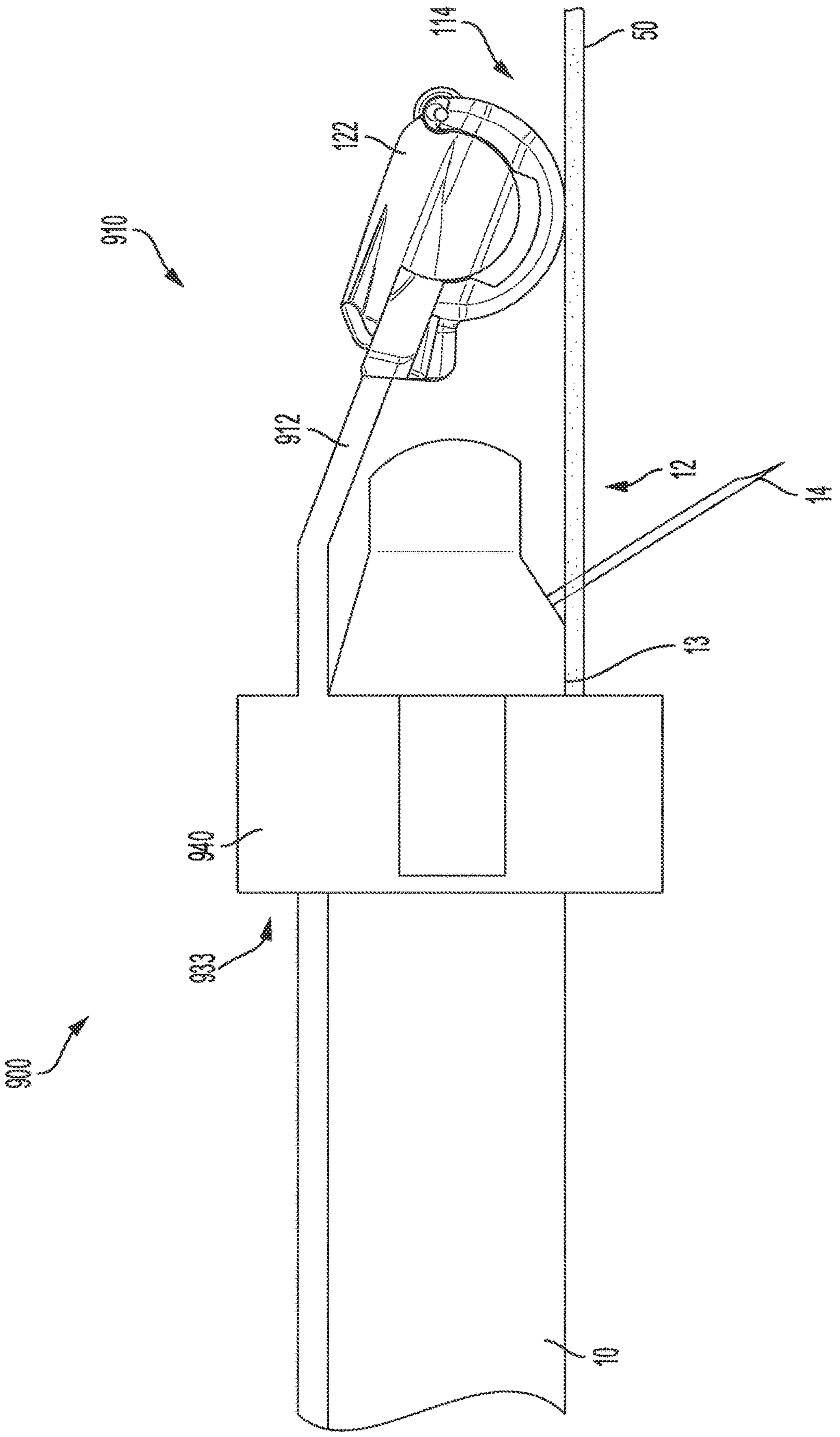
FIG. 11 illustrates a side view of an ultrasonic attachment assembly positioned on the distal end of a duodenoscope, according to at least one non-limiting aspect of this disclosure.

Referring now to FIG. 11, an ultrasonic attachment assembly 900 is shown positioned on the distal end 12 of the duodenoscope 10. The ultrasonic attachment assembly 900 includes a sleeve 940 and a ultrasonic transducer 910. The sleeve 940 includes a cavity 933. The ultrasonic transducer includes the transducer lens 114 and a transducer body 912.

According to the non-limiting aspect of FIG. 11, the sleeve 940 and the transducer body 912 are both constructed from an elastomeric material having a high durometer, such as the elastomeric materials having a high durometer described above. As shown in FIG. 11, the sleeve 940 and the transducer body 912 are formed as a single piece. In other aspects, the sleeve 940 and the transducer body 912 may be two separate pieces.

The sleeve 940 can be similar in many respects to the sleeve 640. When the sleeve 940 is placed over the distal end 12 of the duodenoscope 10, the transducer body 912 is positioned such that the transducer lens 114 is positioned distally with respect to the distal end 12 of the duodenoscope 10. Further, the sleeve 940 and the transducer body 912 can be configured to laterally position the transducer lens 114 with respect to the duodenoscope 10. As explained above with respect to FIG. 3D, the elevator channel 18 axis EA is offset from the center axis CA of the duodenoscope 10. The sleeve 940 and the transducer body 912 can be configured such that the axis UA (not shown in FIG. 11) defining the center of the field of view of the transducer lens 114 laterally aligns with the elevator channel 18 axis EA rather than the center axis CA of the duodenoscope 10. Laterally aligning the axis UA with the elevator channel 18 axis EA can ensure that the ultrasonic image captured by the ultrasonic transducer 910 is centered on the various instruments advanced from the duodenoscope 10.

Figure 12:
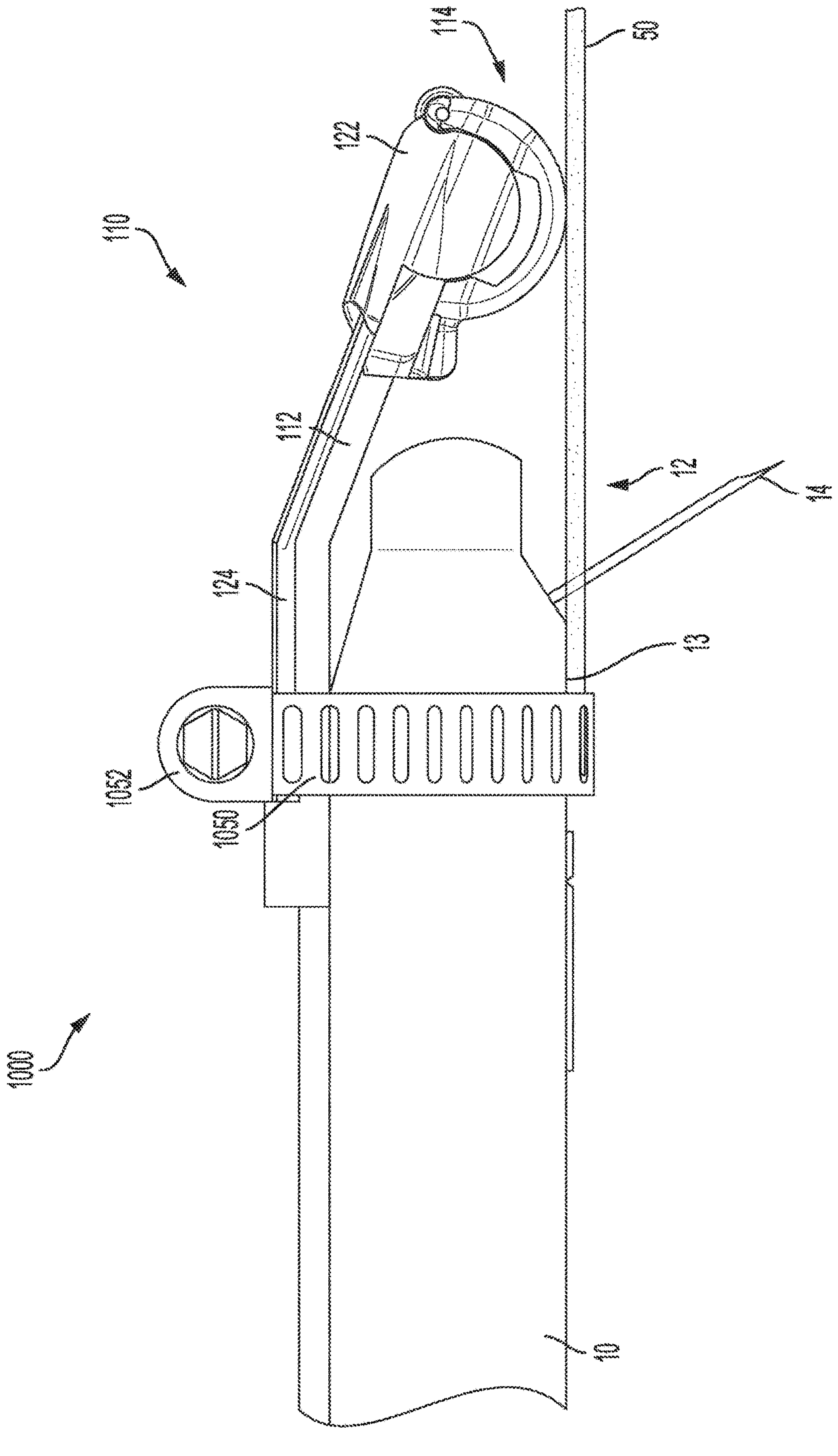
FIG. 12 illustrates a side view of an ultrasonic attachment assembly positioned on the distal end of a duodenoscope, according to at least one non-limiting aspect of this disclosure.

Referring now to FIG. 12, an ultrasonic attachment assembly 1000 is shown positioned on the distal end 12 of the duodenoscope 10. Similar to the ultrasonic attachment assembly 100 above, the ultrasonic assembly 1000 can include the ultrasonic transducer 110 and the spine 124. The ultrasonic attachment assembly 1000 can further include a clamp 1050.

The clamp 1050 is similar in many respects to the sleeve 640. For example, the clamp 1050 is configured fit around the distal end 12 of the duodenoscope 10 and removably secure the ultrasonic transducer 110 to the duodenoscope 10. The clamp 1050 may include a protrusion that extends into the elevator channel 18 as the clamp 1050 is slid over the duodenoscope 10 (not shown in FIG. 12) to axially and rotationally position the clamp 1050 with respect to the distal end 12 of the duodenoscope 10, similar to the protrusion 642 described above.

Still referring to FIG. 12, in some aspects, the clamp 1050 can include features similar to the clip 130 described above with respect to FIGS. 3A-3D. For example, the clamp 1050 can be configured to laterally position the transducer lens 114 with respect to the duodenoscope 10. As explained above with respect to FIG. 3D, the elevator channel 18 axis EA is offset from the center axis CA of the duodenoscope 10. The clamp 1050 can be configured such that the axis UA (not shown in FIG. 12) defining the center of the field of view of the transducer lens 114 laterally aligns with the elevator channel 18 axis EA rather than the center axis CA of the duodenoscope 10. Laterally aligning the axis UA with the elevator channel 18 axis EA can ensure that the ultrasonic image captured by the ultrasonic transducer 110 is centered on the various instruments advanced from the duodenoscope 10.

In some aspects, the clamp 1050 can include a mechanism 1052 configured to secure the clamp 1050 to the duodenoscope such that that clamp 1050 and the ultrasonic transducer 110 do not become dislodged or misaligned during an endoscopic procedure. For example, the mechanism 1052 may include a worm drive (as shown in FIG. 12) or a ratcheting mechanism (not shown).

Figure 13:
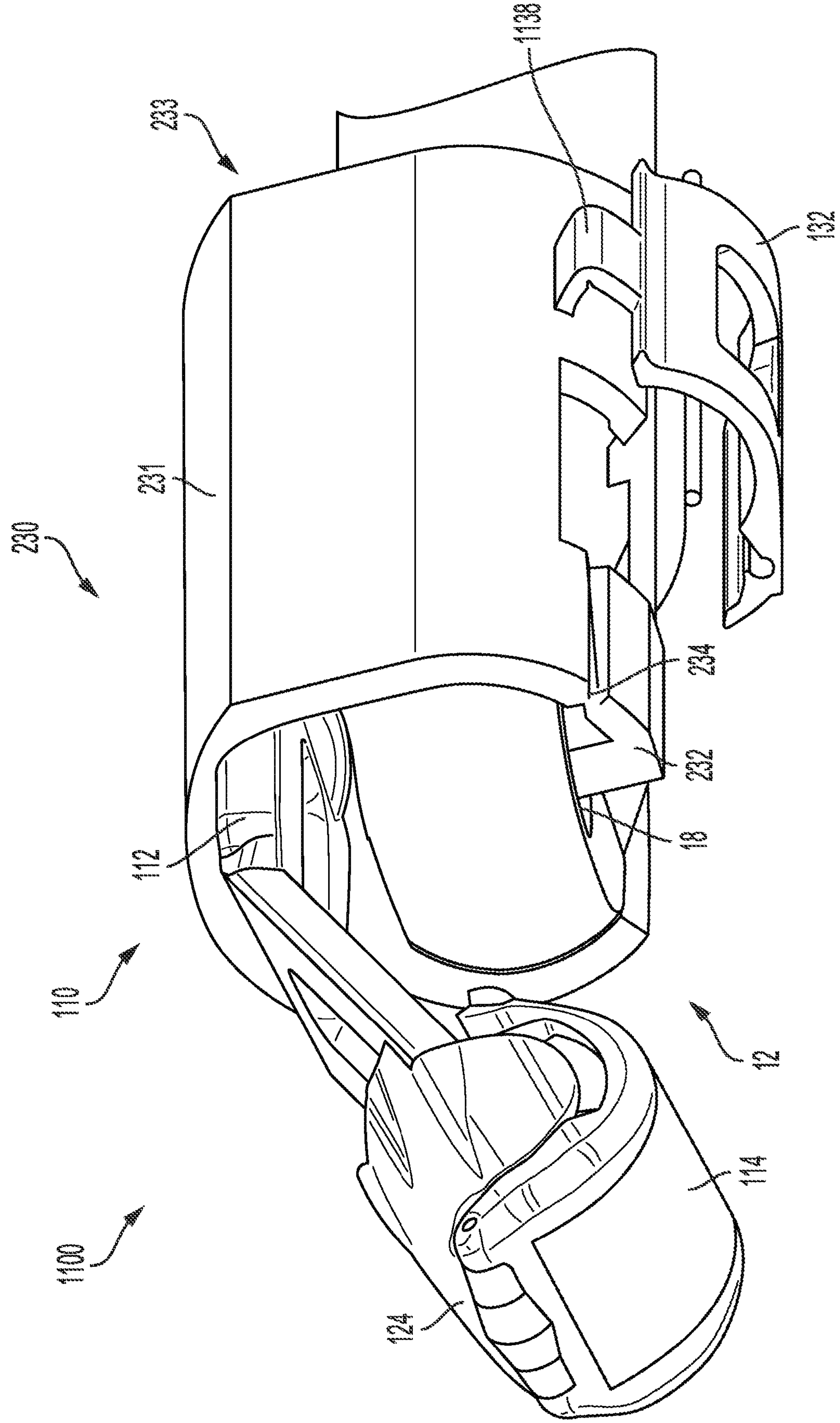
FIG. 13 illustrates a side view of an ultrasonic attachment assembly positioned on the distal end of a duodenoscope, according to at least one non-limiting aspect of this disclosure.

Referring now to FIG. 13, an ultrasonic attachment assembly 1100 is shown positioned on the distal end 12 of the duodenoscope 10. The ultrasonic attachment assembly 1100 is similar in many respects to the ultrasonic attachment assembly 200 described above with respect to FIGS. 4A-4B.

The ultrasonic attachment assembly 1100 includes the ultrasonic transducer 110 and the clip 230. In the non-limiting aspect of FIG. 13, the hinge 132 includes a living hinge 1138.

Figure 14A:
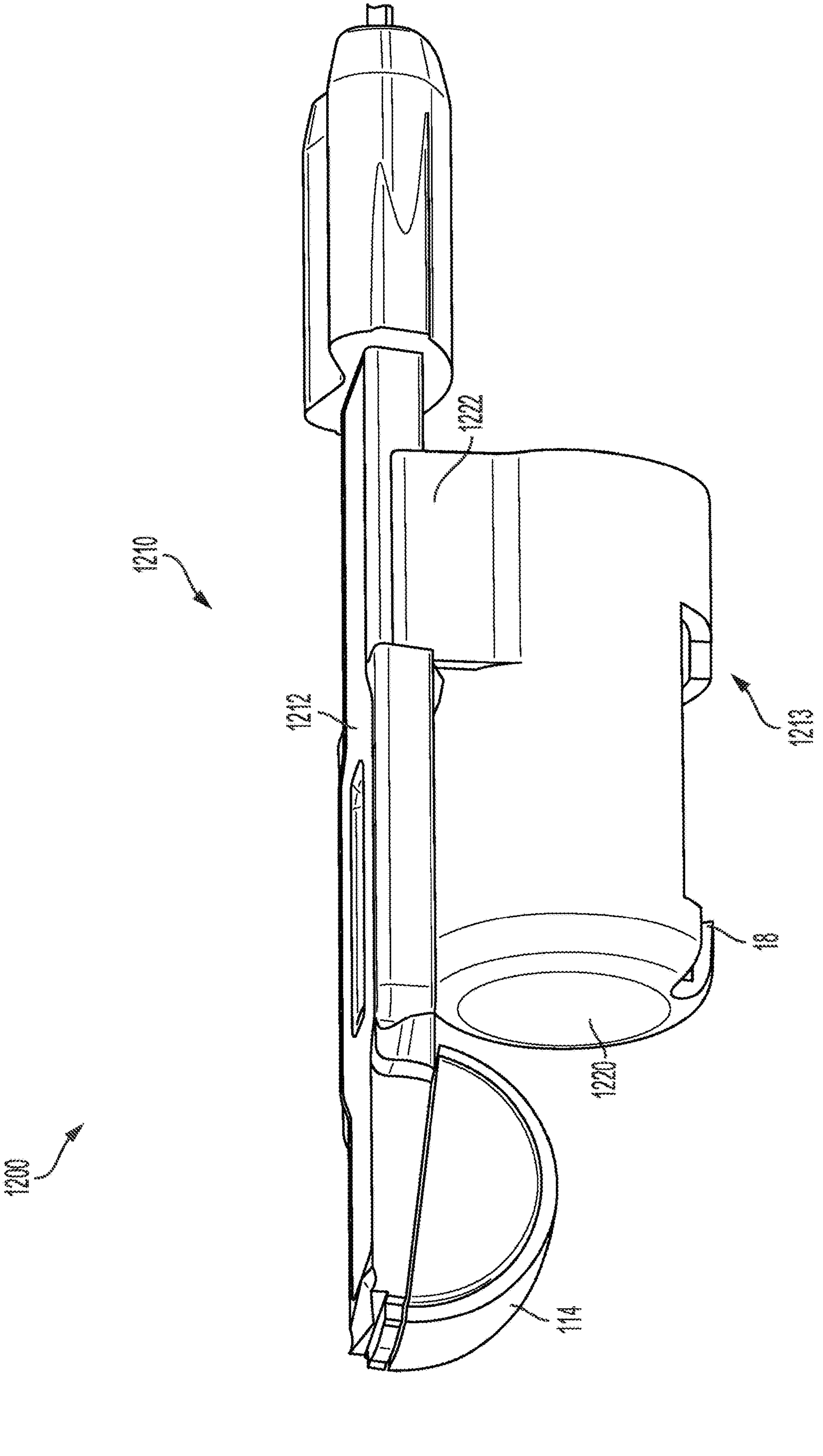
FIGS. 14A-14B illustrate perspective views of an ultrasonic attachment assembly, including a transducer attachment cap, according to several non-limiting aspects of this disclosure.
Figure 14B:
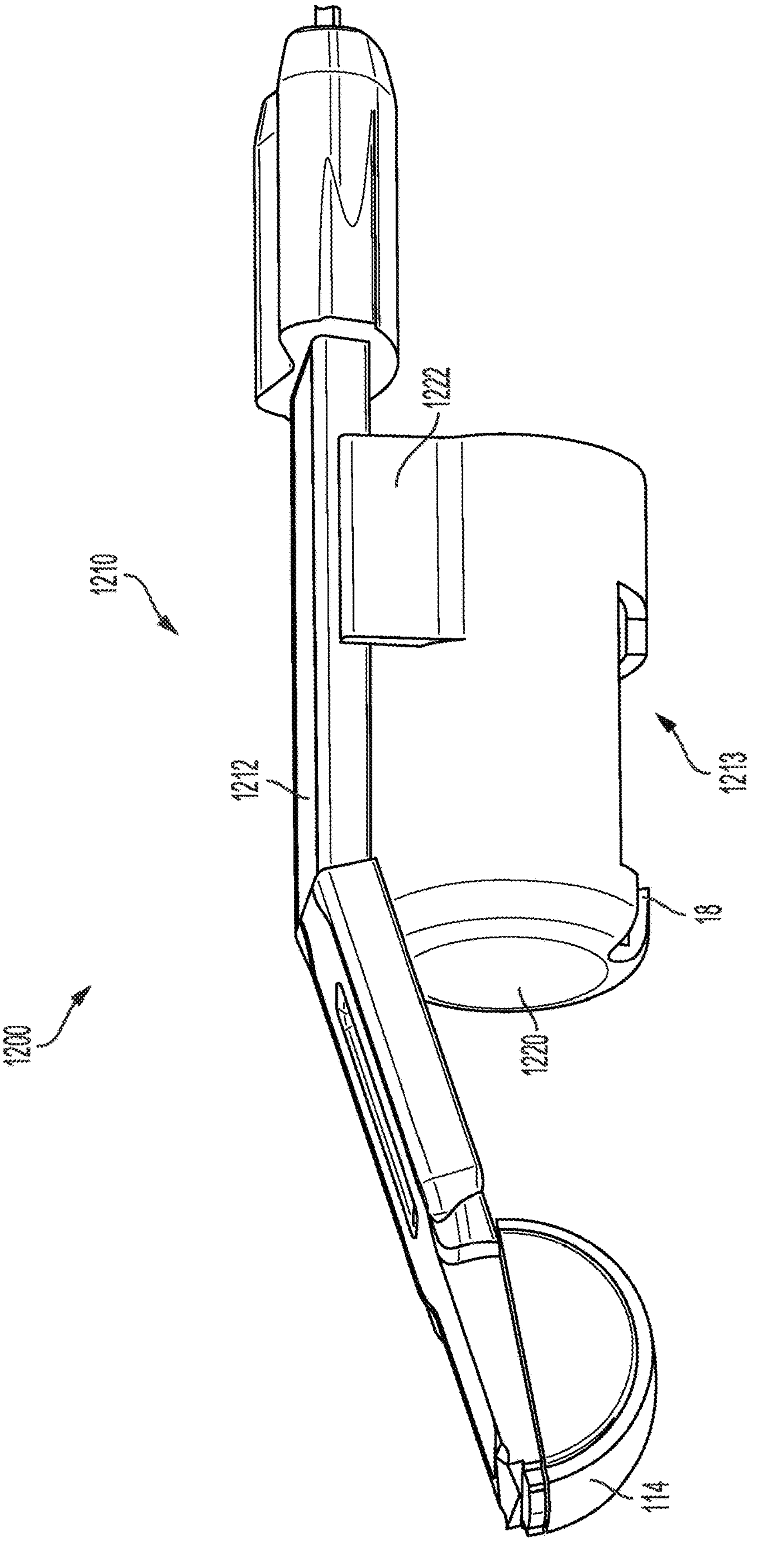

FIGS. 14A-B illustrate a perspective view of an ultrasonic attachment assembly 1200, according to at least one non-limiting aspect of this disclosure. The ultrasonic attachment assembly 1200 includes an ultrasonic transducer 1210 and a transducer attachment cap 1220.

The ultrasonic transducer 1210 includes a transducer body 1212 and the transducer lens 114. The ultrasonic transducer 1210 can be similar in many respects to the ultrasonic transducer 110 and/or the ultrasonic transducer 410 described above. For example, the transducer body 1212 may be constructed from an elastomeric material, an elastomeric material having a high durometer, and/or a rigid plastic material. Further, in some aspects, the ultrasonic attachment assembly may include a spine (not shown) similar to the spine 124 and/or the spine 724.

Referring primarily to FIGS. 14A-14B, and also to FIG. 2, the transducer attachment cap 1220 can be similar in many respects to the removable cap 32. For example, the transducer attachment cap 1220 can include an elevator channel 18 and elevator mechanism 20 (not shown in FIGS. 14A-14B). Further, the transducer attachment cap 1220 can be configured to attach to the distal end 12 of the of the duodenoscope 30. Also similar to the removable cap 32, the transducer attachment cap 1220 can be disposable. Thus, a new transducer attachment cap 1220 can be used for each procedure that is performed using the duodenoscope 30. Accordingly, using the transducer attachment cap 1220 can eliminate various difficulties associated with cleaning the elevator mechanism 20 and other small spaces defined by the duodenoscope 30.

In some aspects, the transducer attachment cap 1220 can be constructed from a rigid plastic material, such as the rigid plastic materials disclosed herein. In other aspects, the transducer attachment cap 1220 can be constructed from an elastomeric material having a high durometer, such as the elastomeric materials having a high durometer disclosed herein.

The transducer attachment cap 1220 can be configured to hold the transducer body 1212 such that the transducer lens 114 is positioned distally with respect to the distal end 12 of the duodenoscope 30 when the transducer attachment cap 1220 is attached to the distal end 12 of the duodenoscope 30. For example, the transducer attachment cap 1220 can include channel 1222 configured to hold the transducer body 1212. In some aspects, the channel 1222 can be configured to secure the transducer body 1212 via friction and/or a snap-in-place-type mechanism. In other aspects, the transducer attachment cap 1220 can include a hinge configured to secure the transducer body 1212 to the transducer attachment cap 1220, for example, similar to the hinge 132 described above.

Still referring primarily to FIGS. 14A-14B, and also to FIG. 2, the transducer attachment cap 1220 can be configured to laterally position the transducer lens 114 with respect to the duodenoscope 30. For example, as explained above with respect to the duodenoscope 10 of FIG. 3D, the elevator channel 18 axis EA is offset from the center axis CA of the duodenoscope 10. Likewise, when the transducer attachment cap 1220 is placed on the distal end of the duodenoscope 30, the elevator channel 18 axis can be similarly offset from the center axis of the duodenoscope 30. Accordingly, the transducer attachment cap 1220 can be configured such that, when the transducer attachment cap 1220 is on the duodenoscope 30 and the ultrasonic transducer 1210 is attached to the transducer attachment cap 1220, the axis defined by the center of the field of view of the transducer lens 114 laterally aligns with the elevator channel 18 axis rather than the center axis of the duodenoscope 30. Laterally aligning the axis defined by the center of the field of view of the transducer lens 114 with the elevator channel 18 axis can ensure that the ultrasonic image captured by the ultrasonic transducer 1210 is centered on the various instruments advanced from the duodenoscope 30.

Referring now to FIG. 14B, in some aspects the transducer body 1212 can be configured such the transducer lens 114 is positioned to contact and acoustically couple with patient tissue 50 during a procedure. For example, the transducer attachment cap 1220 can include a front face 1213 (e.g., the side of the transducer attachment cap 1220 that includes the elevator channel 18). The front face 1213 can define a front-face plane. The transducer body 1212 can be configured to position the transducer lens 114 substantially along the same plane as the front face 13 of the transducer attachment cap 1220. Thus, maneuvering the duodenoscope 30 such that the front face 1213 of the transducer attachment cap 1220 is in contact with patient tissue 50 may also cause the transducer lens 114 to be in contact with the patient tissue 50, thereby acoustically coupling the transducer lens 114 with the patient tissue 50.

In the non-limiting aspect of FIG. 14B, the transducer body 1212 is formed to include a bend configured to position the transducer lens 114 substantially along the same plane as the front face 1213 of the transducer attachment cap 1220. Thus, the ultrasonic attachment assembly 1200 may not include a rigid plastic spine, such as the spine 124 described above with respect to FIGS. 3A-3D. In other aspects, the ultrasonic attachment assembly 1200 may include a rigid plastic spine configured to position the transducer lens 114 for acoustic coupling, such as the spine 124 described above with respect to FIGS. 3A-3D.

In some aspects, various components of the ultrasonic attachment assemblies disclosed herein may be intended for a single use. For example, the clip 133, the sleeve 140, and/or the spine 124 of ultrasonic attachment assembly 100 (and similar components of other ultrasonic attachment assemblies) may be disposed of after a single endoscopic procedure whereas the ultrasonic transducer 110 can be cleaned and sanitized for reuse. Thus, various ultrasonic attachment assemblies described herein may be configured for easy cleaning and sanitation by employing disposable components.

In some aspects, various components of the ultrasonic attachment assemblies described herein can be configured to maintain a minimum overall outer diameter (i.e., a minimum outer profile). For example, various procedures may require that the distal end 12 of the duodenoscope 10 and any ultrasonic attachment assembly attached thereto be able to fit through a minimum sphincter size (e.g., a sphincter size of no greater than 18 mm). Further, the materials used to construct the various components described herein, such as the clip 133, the sleeve 140, and/or the spine 124 of ultrasonic attachment assembly 100 (and similar components of other ultrasonic attachment assemblies), may require a minimum wall thickness for structural integrity. Accordingly, as described above, various components of the ultrasonic attachment assemblies described herein may be combined and formed as a single piece to eliminate the use of multiple components each requiring a minimum wall thickness, thereby minimizing the overall outer diameter of the resulting ultrasonic attachment assembly. For example, as described with respect to FIG. 7, the transducer body 512 and the clip 530 of the ultrasonic assembly 500 are formed as a single piece. Accordingly, the ultrasonic assembly 500 may have as smaller overall outer diameter compared to a similar ultrasonic assembly that has a separate transducer body and clip. As another example, as described with respect to FIG. 11, the sleeve 940 and the transducer body 912 of ultrasonic attachment assembly 900 may be formed as a single piece. Accordingly, the ultrasonic assembly 900 may have as smaller overall outer diameter compared to a similar ultrasonic assembly that has a separate transducer body and clip.

Various aspects of the devices, systems, and methods described herein are set out in the following clauses.

Clause 1. An ultrasonic attachment assembly, comprising: an ultrasonic transducer comprising a transducer lens and a transducer body; and a clip configured to be removably secured to a distal end of an endoscope, wherein the clip comprises: a clip body; and a cavity formed in the clip body, wherein the cavity is configured to hold the transducer body when the clip is secured to the distal end of the endoscope such that the transducer lens is positioned distally with respect to the distal end of the endoscope.

Clause 2. The ultrasonic attachment of Clause 1, wherein the endoscope is a duodenoscope comprising an elevator channel.

Clause 3. The ultrasonic attachment assembly of any of Clauses 1-2, further comprising: a sleeve configured to slide around the distal end of the duodenoscope, wherein the sleeve comprises a tab extending radially therefrom, wherein the clip is configured to be placed over the sleeve to position the clip on the distal end of the endoscope, and wherein the clip further comprises an opening formed in the clip body, the opening configured for the tab to extend therethrough when the clip is placed over the sleeve to axially and rotationally position the clip with respect to the sleeve.

Clause 4. The ultrasonic attachment assembly of any of Clauses 1-3, wherein the sleeve further comprises a protrusion configured to extend into the elevator channel when the sleeve is slid around the distal end of the duodenoscope to axially and rotationally position the sleeve with respect to the duodenoscope.

Clause 5. The ultrasonic attachment assembly of any of Clauses 1-4, wherein the sleeve comprises an elastomeric material.

Clause 6. The ultrasonic attachment assembly of any of Clauses 1-5, wherein the clip further comprises a protrusion configured to extend into the elevator channel to axially and rotationally position the clip with respect to the distal end of the duodenoscope.

Clause 7. The ultrasonic attachment assembly of any of Clauses 1-6, wherein the duodenoscope comprises a central axis, wherein the elevator channel defines an elevator channel axis that is offset from the central axis, wherein the transducer lens comprises a field of view, and wherein the cavity is configured such that the field of view is centered along the elevator channel axis when the cavity holds the transducer body.

Clause 8. The ultrasonic attachment assembly of any of Clauses 1-7, wherein the duodenoscope comprises a front face, wherein the front face defines a front face plane, wherein the transducer lens is positioned substantially along the front face plane when the cavity holds the transducer body, and wherein positioning the transducer lens substantially along the front face plane enables the transducer lens to acoustically couple with patient tissue when the front face of the duodenoscope is placed against the patient tissue.

Clause 9. The ultrasonic attachment assembly of any of Clauses 1-8, wherein the transducer body comprises an elastomeric material, and wherein the ultrasonic attachment assembly further comprises: a spine comprising a rigid plastic material, wherein the spine is configured to position the transducer body such that the transducer lens is positioned substantially along the front face plane when the cavity holds the transducer body.

Clause 10. The ultrasonic attachment assembly of any of Clauses 1-9, wherein the clip comprises the rigid plastic material, and wherein the spine and the clip are formed as a single piece.

Clause 11. The ultrasonic attachment assembly of any of Clauses 1-10, wherein the transducer body comprises a rigid plastic material, and wherein the transducer body is configured to position the transducer lens substantially along the front face plane when the cavity holds the transducer body.

Clause 12. The ultrasonic attachment assembly of any of Clauses 1-11, wherein the clip comprises the rigid plastic material, and wherein the transducer body and the clip are formed as a single piece.

Clause 13. The ultrasonic attachment assembly of any of Clauses 1-12, wherein the clip comprises a hinge configured to removably secure the clip to the distal end of the duodenoscope, and wherein the hinge comprises at least one of: a living hinge; or a knuckle and a pin.

Clause 14. An ultrasonic attachment assembly, comprising an ultrasonic transducer comprising a transducer lens and a transducer body; and a sleeve configured to be positioned on a distal end of an endoscope by removably sliding the sleeve over the distal end of the endoscope, wherein the sleeve is configured to hold the transducer body when the sleeve is positioned on the distal end of the endoscope such that the transducer lens is positioned distally with respect to the distal end of the endoscope.

Clause 15. The ultrasonic attachment of Clause 14, wherein the endoscope is a duodenoscope comprising an elevator channel.

Clause 16. The ultrasonic attachment assembly of any of Clauses 14-15, wherein the sleeve comprises a protrusion configured to extend into the elevator channel when the sleeve is slid around the distal end of the duodenoscope to axially and rotationally position the sleeve with respect to the distal end of the duodenoscope.

Clause 17. The ultrasonic attachment assembly of any of Clauses 14-16, wherein the duodenoscope comprises a central axis, wherein the elevator channel defines an elevator channel axis that is offset from the central axis, wherein the transducer lens comprises a field of view, and wherein the sleeve is configured such that the field of view is centered along the elevator channel axis when the sleeve holds the transducer body.

Clause 18. The ultrasonic attachment assembly of any of Clauses 14-17, wherein the duodenoscope comprises a front face, wherein the front face defines a front face plane, wherein the transducer lens is positioned substantially along the front face plane when the sleeve holds the transducer body, and wherein positioning the transducer lens substantially along the front face plane enables the transducer lens to acoustically couple with patient tissue when the front face of the duodenoscope is placed against the patient tissue.

Clause 19. The ultrasonic attachment assembly of any of Clauses 14-18, wherein the transducer body comprises an elastomeric material, and wherein the ultrasonic attachment assembly further comprises: a spine configured to position the transducer body such that the transducer lens is positioned substantially along the front face plane when the cavity holds the transducer body.

Clause 20. The ultrasonic attachment assembly of any of Clauses 14-19, wherein the spine comprises a rubber material.

Clause 21. The ultrasonic attachment assembly of any of Clauses 14-19, wherein the spine comprises a rigid plastic material.

Clause 22. The ultrasonic attachment assembly of any of Clauses 14-18, wherein the sleeve comprises a first elastomeric material, and wherein the transducer body comprises a second elastomeric material.

Clause 23. The ultrasonic attachment assembly of Clause 22, wherein the first elastomeric material and the second elastomeric material are the same, and wherein the sleeve and the transducer body are formed as a single piece.

Clause 24. The ultrasonic attachment assembly of any of Clauses 14-23, wherein the transducer body comprises a rigid plastic material.

Clause 25. An ultrasonic attachment assembly, comprising: an ultrasonic transducer comprising a transducer lens and a transducer body; and a transducer attachment cap configured to removably attach to a distal end of a duodenoscope, wherein the distal end of the duodenoscope is configured to accept a disposable cap, wherein the transducer attachment cap can be used instead of the disposable cap, and wherein the transducer attachment cap is configured to hold the transducer body such that the transducer lens is positioned distally with respect to the distal end of the duodenoscope when the transducer attachment cap is attached to the distal end of the duodenoscope.

Clause 26. The ultrasonic attachment assembly of Clause 25, wherein the transducer attachment cap comprises an elevator channel, wherein the duodenoscope comprises a central axis, wherein the elevator channel defines an elevator channel axis that is offset from the central axis when the transducer attachment cap is attached to the duodenoscope, wherein the transducer lens comprises a field of view, and wherein the transducer attachment cap is configured such that the field of view is centered along the elevator channel axis when the transducer attachment cap holds the transducer body.

Clause 27. The ultrasonic attachment assembly of any of Clauses 25-26, wherein the transducer attachment cap comprises a front face, wherein the front face defines a front face plane, wherein the transducer lens is positioned substantially along the front face plane when the transducer attachment cap holds the transducer body, and wherein positioning the transducer lens substantially along the front face plane enables the transducer lens to acoustically couple with patient tissue when the front face of the transducer attachment cap is placed against the patient tissue.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The term "substantially", "about", or "approximately" as used in the present disclosure, unless otherwise specified, means an acceptable error for a particular value as determined by one of ordinary skill in the art, which depends in part on how the value is measured or determined. In certain embodiments, the term "substantially", "about", or "approximately" means within 1, 2, 3, or 4 standard deviations. In certain embodiments, the term "substantially", "about", or "approximately" means within 50%, 20%, 15%, 10%, 9%, 8%, 7%, 6%, 5%, 4%, 3%, 2%, 1%, 0.5%, or 0.05% of a given value or range.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. An ultrasonic attachment assembly, comprising:

an ultrasonic transducer comprising:

a transducer lens comprising a field of view; and a transducer body; and a clip configured to be removably secured to a distal end of a duodenoscope comprising an elevator channel, wherein the distal end of the duodenoscope defines a central axis, wherein the elevator channel defines an elevator channel axis that is offset from the central axis, and wherein the clip comprises:

a clip body; and a cavity formed in the clip body, wherein the cavity is configured to selectively engage the transducer body when the clip is secured to the distal end of the duodenoscope such that the transducer lens is positioned distally with respect to the distal end of the duodenoscope and such that the field of view is centered along the elevator channel axis.

2. The ultrasonic attachment assembly of claim 1, wherein the clip further comprises a protrusion configured to extend into the elevator channel to axially and rotationally position the clip with respect to the distal end of the duodenoscope.

3. The ultrasonic attachment assembly of claim 1, wherein the distal end of the duodenoscope comprises a front face, wherein the front face defines a front face plane, wherein the transducer lens is positioned substantially along the front face plane when the cavity holds the transducer body, and wherein positioning the transducer lens substantially along the front face plane enables the transducer lens to acoustically couple with patient tissue when the front face of the duodenoscope is placed proximate to the patient tissue.

4. The ultrasonic attachment assembly of claim 3, wherein the transducer body comprises an elastomeric material, and wherein the ultrasonic attachment assembly further comprises:

a spine comprising a rigid plastic material, wherein the spine extends along the transducer body and is configured to position the transducer body such that the transducer lens is positioned substantially along the front face plane when the cavity holds the transducer body.

5. The ultrasonic attachment assembly of claim 4, wherein the clip comprises the rigid plastic material, and wherein the spine and the clip are formed as a single piece.

6. The ultrasonic attachment assembly of claim 3, wherein the transducer body comprises a rigid plastic material, and wherein the transducer body is configured to position the transducer lens substantially along the front face plane when the cavity holds the transducer body.

7. The ultrasonic attachment assembly of claim 6, wherein the clip comprises the rigid plastic material, and wherein the transducer body and the clip are formed as a single piece.

8. The ultrasonic attachment assembly of claim 1, wherein the clip comprises a hinge configured to removably secure the clip to the distal end of the duodenoscope, and wherein the hinge comprises at least one of:

a living hinge; or a knuckle and a pin.

9. An ultrasonic attachment assembly, comprising:

an ultrasonic transducer comprising:

a transducer lens comprising a field of view; and a transducer body:

a clip configured to be removably secured to a distal end of a duodenoscope comprising an elevator channel, wherein the distal end of the duodenoscope defines a central axis, wherein the elevator channel defines an elevator channel axis that is offset from the central axis, and wherein the clip comprises:

a clip body; and a cavity formed in the clip body, wherein the cavity is configured to hold the transducer body when the clip is secured to the distal end of the duodenoscope such that the transducer lens is positioned distally with respect to the distal end of the duodenoscope and such that the field of view is centered along the elevator channel axis; and a sleeve configured to slide around the distal end of the duodenoscope, wherein the sleeve comprises a tab extending radially therefrom, wherein the clip is configured to be placed over the sleeve to position the clip on the distal end of the duodenoscope, and wherein the clip further comprises an opening formed in the clip body, the opening configured for the tab to extend therethrough when the clip is placed over the sleeve to axially and rotationally position the clip with respect to the sleeve.

10. The ultrasonic attachment assembly of claim 9, wherein the sleeve further comprises a protrusion configured to extend into the elevator channel when the sleeve is slid around the distal end of the duodenoscope to axially and rotationally position the sleeve with respect to the duodenoscope.

11. The ultrasonic attachment assembly of claim 10, wherein the sleeve comprises an elastomeric material.

12. An ultrasonic attachment assembly, comprising:

an ultrasonic transducer comprising:

a transducer lens comprising a field of view; and a transducer body; and a sleeve configured to be positioned on a distal end of a duodenoscope by removably sliding the sleeve over the distal end of the duodenoscope, wherein the duodenoscope comprises an elevator channel, wherein the distal end of the duodenoscope defines a central axis, wherein the elevator channel defines an elevator channel axis that is offset from the central axis, wherein the sleeve is configured to selectively engage the transducer body when the sleeve is positioned on the distal end of the duodenoscope such that the transducer lens is positioned distally with respect to the distal end of the duodenoscope and such that that the field of view is centered along the elevator channel axis.

13. The ultrasonic attachment assembly of claim 12, wherein the sleeve comprises a protrusion configured to extend into the elevator channel when the sleeve is slid over the distal end of the duodenoscope to axially and rotationally position the sleeve with respect to the distal end of the duodenoscope.

14. The ultrasonic attachment assembly of claim 12, wherein the distal end of the duodenoscope comprises a front face, wherein the front face defines a front face plane, wherein the transducer lens is positioned substantially along the front face plane when the sleeve holds the transducer body, and wherein positioning the transducer lens substantially along the front face plane enables the transducer lens to acoustically couple with patient tissue when the front face of the duodenoscope is placed proximate to the patient tissue.

15. The ultrasonic attachment assembly of claim 14, wherein the transducer body comprises an elastomeric material, and wherein the ultrasonic attachment assembly further comprises:

a spine extending along the transducer body and configured to position the transducer body such that the transducer lens is positioned substantially along the front face plane when the sleeve holds the transducer body.

16. The ultrasonic attachment assembly of claim 15, wherein the spine comprises a rubber material.

17. The ultrasonic attachment assembly of claim 15, wherein the spine comprises a rigid plastic material.

18. The ultrasonic attachment assembly of claim 14, wherein the sleeve comprises a first elastomeric material, and wherein the transducer body comprises a second elastomeric material.

19. The ultrasonic attachment assembly of claim 18, wherein the first elastomeric mater and the second elastomeric material are the same, and wherein the sleeve and the transducer body are formed as a single piece.

20. The ultrasonic attachment assembly of claim 14, wherein the transducer body comprises a rigid plastic material.

* * * * *